(12) United States Patent
Mathiowitz et al.

(10) Patent No.: US 7,029,700 B2
(45) Date of Patent: Apr. 18, 2006

(54) MICRONIZED FREEZE-DRIED PARTICLES

(75) Inventors: Edith Mathiowitz, Brookline, MA (US); Yong S. Jong, Providence, RI (US); Jules S. Jacob, Taunton, MA (US)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 09/760,046

(22) Filed: Jan. 12, 2001

(65) Prior Publication Data

US 2003/0082236 A1 May 1, 2003

Related U.S. Application Data

(60) Provisional application No. 60/176,193, filed on Jan. 14, 2000.

(51) Int. Cl.
*A61K 9/14* (2006.01)
*A61K 9/50* (2006.01)

(52) U.S. Cl. ........................ 424/489; 424/499
(58) Field of Classification Search ................ 424/489, 424/490, 499
See application file for complete search history.

(56) References Cited

U.S. PATENT DOCUMENTS

| | | | |
|---|---|---|---|
| 4,151,273 A | 4/1979 | Riegelman et al. |
| 4,332,721 A | 6/1982 | Bernini et al. |
| 4,384,975 A | 5/1983 | Fong et al. |
| 4,757,128 A | 7/1988 | Domb et al. |
| 4,997,904 A | 3/1991 | Domb |
| 5,043,280 A | 8/1991 | Fischer et al. |
| 5,175,235 A | 12/1992 | Domb et al. |
| 5,354,562 A | 10/1994 | Platz et al. |
| 5,407,609 A | 4/1995 | Tice et al. |
| 5,639,441 A | 6/1997 | Sievers et al. |
| 5,667,808 A | 9/1997 | Johnson et al. |

(Continued)

FOREIGN PATENT DOCUMENTS

EP 0 225 162 A 6/1987

(Continued)

OTHER PUBLICATIONS

Kornblum, "Sustained-action tablets prepared by employing a spray-drying technique for granulation," *J Pharm Sci* 58(1):125-27 (1969).

(Continued)

*Primary Examiner*—Thurman K. Page
*Assistant Examiner*—Humera N. Sheikh
(74) *Attorney, Agent, or Firm*—Pabst Patent Group LLP

(57) ABSTRACT

A process is provided for making dry, micronized particles of an agent, such as a drug. The method includes (a) dissolving a macromolecular material, preferably a polymer, in an effective amount of a solvent, to form a solution; (b) dissolving or dispersing the agent in the solution to form a mixture; (c) freezing the mixture; and (d) drying by vacuum the mixture to form solid particles of the agent dispersed in solid macromolecular material. The micronization in this process occurs directly in a macromolecular matrix and hardening of the particles of agent by solvent removal takes place by lyophilization of the bulk matrix, which stabilizes the drug particles during hardening and prevents coalesence, thereby resulting in smaller final drug particles. The method is particularly preferred for protein agents. The process can be used in conjunction with a standard microencapsulation technique, typically following separation of the agent from the macromolecular matrix. The process yields microparticles having a homogenous size distribution, preferably less than 2 μm, and more preferably less than 1 μm, in size. The microparticles have well defined, predictable properties, which is particularly critical in drug delivery applications.

24 Claims, 6 Drawing Sheets

U.S. PATENT DOCUMENTS

| | | |
|---|---|---|
| 5,700,471 A | 12/1997 | End et al. |
| 5,747,002 A | 5/1998 | Clark et al. |
| 5,776,495 A | 7/1998 | Duclos et al. |
| 5,780,062 A | 7/1998 | Frank et al. |
| 5,800,834 A | 9/1998 | Spireas et al. |
| 5,817,343 A | 10/1998 | Burke |
| 5,833,891 A | 11/1998 | Subramaniam et al. |
| 5,851,453 A | 12/1998 | Hanna et al. |
| 5,855,913 A | 1/1999 | Hanes et al. |
| 5,874,029 A | 2/1999 | Subramaniam et al. |
| 5,874,064 A | 2/1999 | Edwards et al. |
| 5,952,008 A | 9/1999 | Backstrom et al. |

FOREIGN PATENT DOCUMENTS

| | | |
|---|---|---|
| WO | WO 97/03657 A | 2/1997 |
| WO | WO 97/03702 A | 2/1997 |
| WO | WO 97/35563 A | 10/1997 |
| WO | 98/46212 * | 10/1998 |
| WO | WO 98/46212 A | 10/1998 |

OTHER PUBLICATIONS

Sawhney, et al., "Bioerodible Hydrogels Based on Photopolymerized Poly(ethylene glycol)-co-poly(a-hydroxy acid) Diacrylate Macromers," *Macromolecules* 26:581-587 (1993).

Tracy, "Development and scale-up of a microsphere protein delivery system," *Biotechnol. Prog* 14:108-15 (1998).

Wehrle, et al., "The influence of process parameters on the PLA nanoparticle size distribution, evaluated by means of factorial design," *European Journal of Pharmaceutics and Biopharmaceuticals* 41(1):19-26 (1995).

* cited by examiner

Figure 2B:
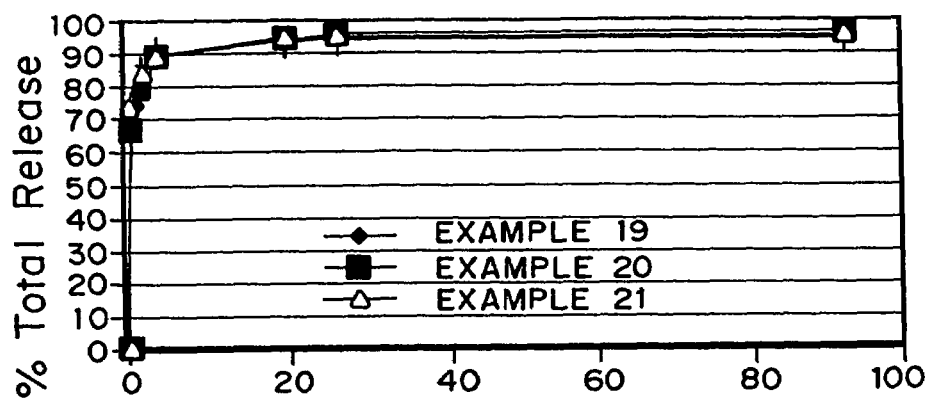
Figure 3A:
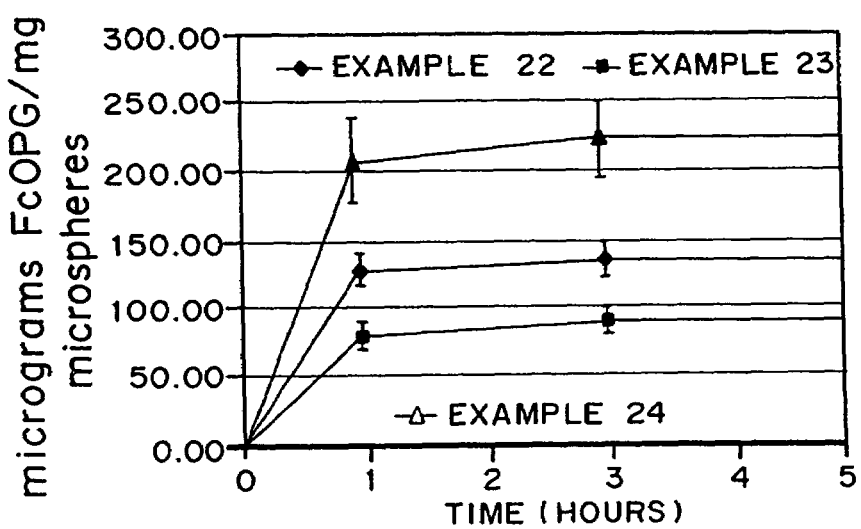
Figure 3B:
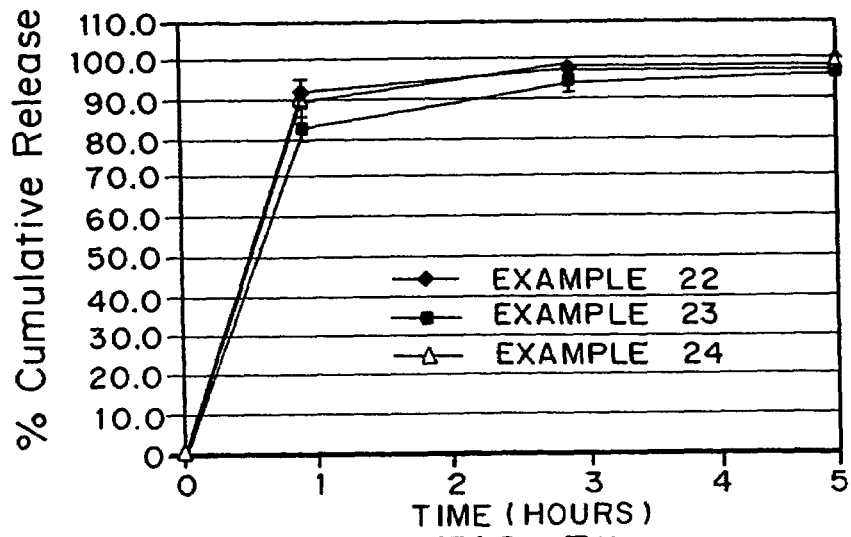
Figure 4A:
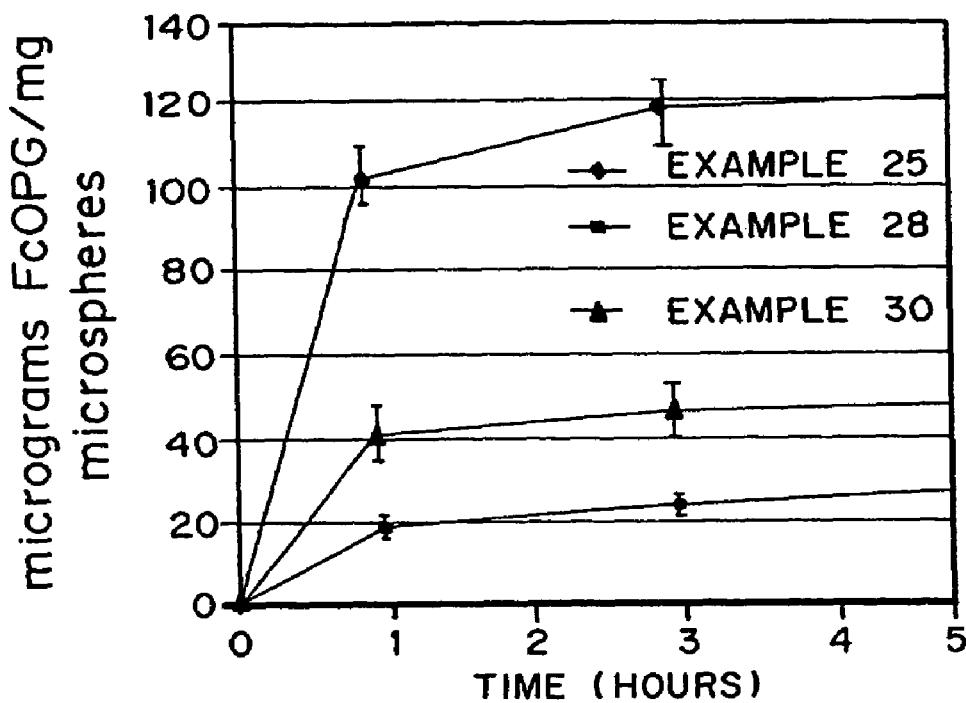
Figure 4B:
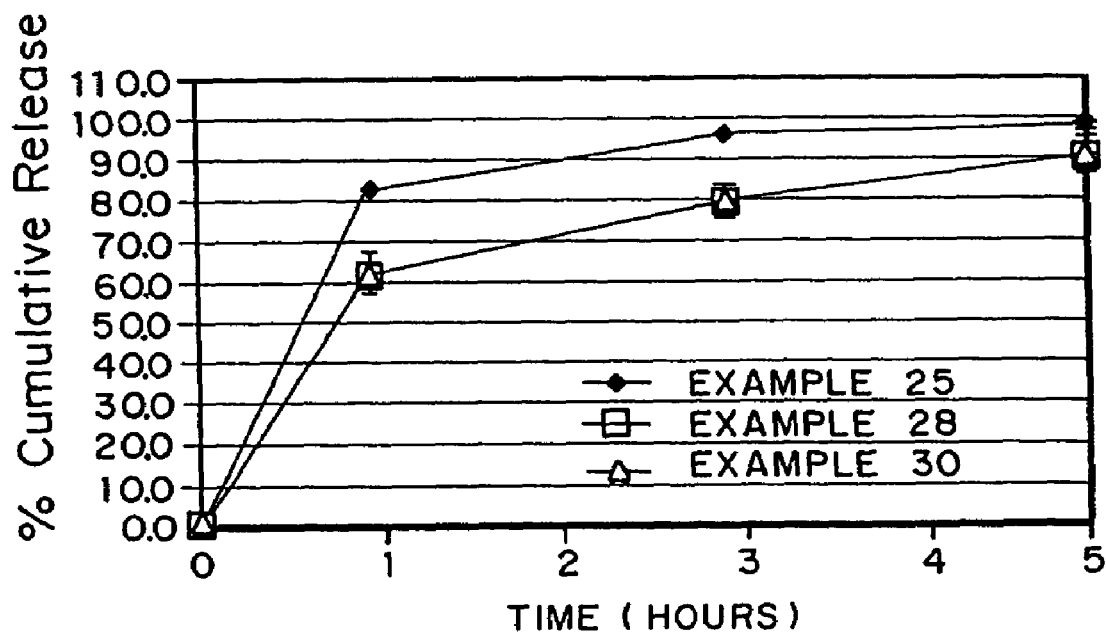

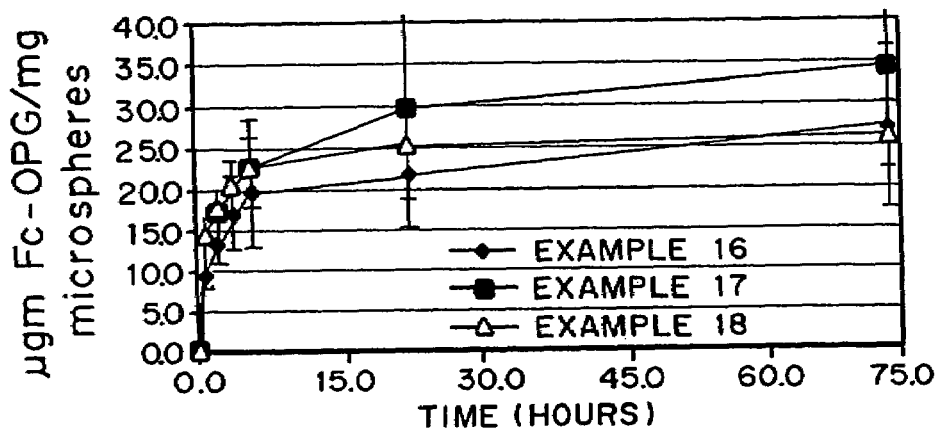
FIG. 1A
FIG. 1B
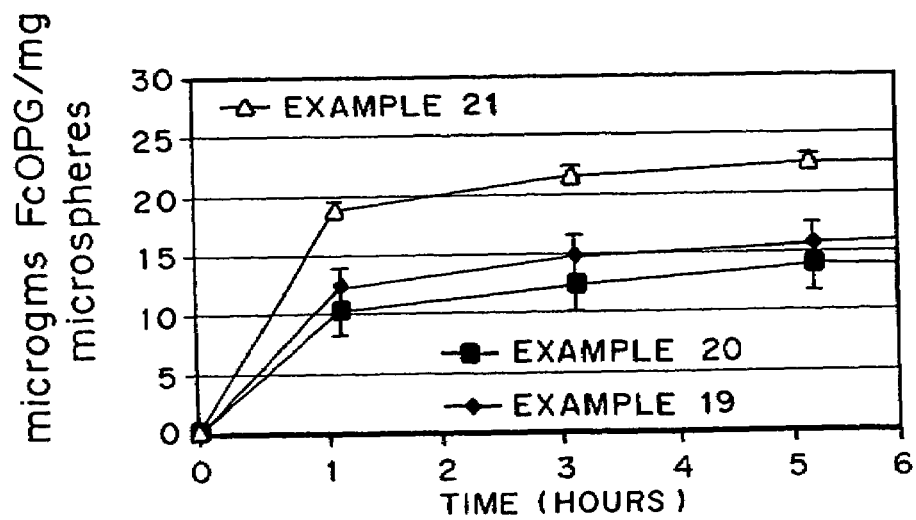
FIG. 2A

MICRONIZED FREEZE-DRIED PARTICLES

This application claims priority to U.S. Ser. No. 60/176,193 filed Jan. 14, 2000.

The United States government has certain rights in this application by virtue of National Institutes of Health grant #1R01GM55245-01.

BACKGROUND OF THE INVENTION

This invention is generally in the field of microencapsulation techniques, particularly for use in the delivery of drugs or other biologically active agents.

Matrix or solid reservoir-type drug delivery systems generally require uniform distribution of drug within the encapsulating material. Proteins can be incorporated into polymer matrices in solution form or as a dry powder. The micronization of proteins and drugs to form solid particles suitable for microencapsulation (e.g., particles having a size less than about 10 µm) has been achieved using a variety of approaches including milling, spray-drying, spray freeze-drying, and supercritical anti-solvent (SAS) precipitation techniques. While proteins are generally more stable in a lyophilized (dry) state than a hydrated state, it is often difficult to produce dry micronized (less than 20 µm) protein particulates. The particle size is critical to drug release kinetics of matrix type devices.

Various milling techniques are known. For example, in U.S. Pat. No. 5,952,008 to Backstrom et al. jet milling is used to reduce the particle size of proteins and polypeptides to produce particles smaller than 10 µm for inhalation administration. U.S. Pat. No. 5,354,562 to Platz et al. discloses solid particle aerosol formulations of polypeptide drugs made by lyophilizing solutions of the drugs which contain milling stabilizers that inhibit degradation of the drug during subsequent milling. The lyophilized drug is milled in fluid energy mills that have been fitted with abrasion resistant materials. The resulting particles are between 0.5 to 4 µm when milled at high pressure and between 4 to 15 µm when milled at low pressure. U.S. Pat. No. 5,747,002 to Clark et al. discloses jet milling of sodium chloride to produce particles with a size distribution smaller than 7 µm. Immediately following the milling, the micronized particles are vacuum dried to prevent aggregation. U.S. Pat. No. 4,151,273 to Riegelman et al. discloses a method for preparing a glassy solid matrix of a carrier and a drug, formed at elevated temperature either with or without added solvent. The matrix is rapidly chilled to form a solid mass and ground to a powder for oral administration in a capsule.

Methods employing supercritical conditions also are well known. For example, U.S. Pat. No. 5,043,280 to Fischer et al. discloses a method for making a pharmaceutical preparation with minimal solvent residue. The method involves introducing a solution (of a substance and a carrier) at a supercritical state into a spray tower to extract a solvent from the sprayed solution to form a sterile product containing the substance embedded in the carrier. U.S. Pat. No. 5,851,453 to Hanna et al. discloses an apparatus to co-inject supercritical fluid and a vehicle containing at least one substance (e.g., drug or protein) in solution or suspension, such that the dispersion and extraction of the vehicle occur simultaneously by action of the supercritical fluid. Microparticulates less than 10 µm are produced. U.S. Pat. No. 5,833,891 to Subramaniam et al. discloses particle precipitation and coating using near-or supercritical fluid conditions. A fluid dispersion with a continuous phase dispersant and a precipitable substance are contacted with supercritical fluid anti-solvent so as to generate focused high frequency anti-solvent sonic waves, which break up the dispersion into extremely small droplets and cause the precipitation of particles between 0.1 and 10 µm in size. U.S. Pat. No. 5,874,029 to Subramaniam et al. discloses using an atomizer nozzle to spray a solvent and solute into a supercritical anti-solvent to cause depletion of the solvent in the droplets and production of nanoparticles in the range of 0.6 µm in size. U.S. Pat. No. 5,639,441 to Sievers et al. discloses producing an aerosol of particles when a solute in solution is mixed with a supercritical antisolvent. The particles are in the size range of 0.1 to 6.5 µm.

Spray drying methods also are well known in the art. For example, U.S. Pat. No. 5,700,471 to End et al. discloses a process for the making fine particles of drug or dye by spray-drying coarse particle dispersions of solutions of the drug or dye at temperatures above the melting point of the active agent. The active agent in solution is mixed with a protective aqueous colloid solution (e.g., consisting of gelatin or lactose) in water heated above the melting point of the drug, resulting in a molten emulsion of the drug in water. The emulsion is spray-dried, resulting in free-flowing powders with particles sizes less than 1 µm. U.S. Pat. No. 5,855,913 to Hanes et al. and U.S. Pat. No. 5,874,064 to Edwards et al. disclose the preparation of aerodynamically light particles between 5 and 30 µm, prepared by spray-drying a therapeutic agent mixed with surfactants or with therapeutic agent mixed with biodegradable polymers. Kornblum, *J. Pharm. Sci.* 58(1):125–27 (1969) discloses spray drying pure drug for purposes of micronization to form spheres in the range of 1–20 µm, and subsequent compression of the spray-dried formulation to produce tablets. Numerous precipitation techniques are also known. For example, U.S. Pat. No. 5,776495 to Duclos et al. discloses the formation of solid dispersions created by co-precipitation via drying of at least one therapeutic agent in an organic solvent with a hydrophilic polymer carrier with at least some solubility in the organic solvent. U.S. Pat. No. 4,332,721 to Bemini et al. discloses a process for preparing a spironolactive by precipitation with water from a solution with organic solvents in the temperature range of 0 to 30° C. U.S. Pat. No. 5,800,834 to Spireas et al discloses the use of systems to produce free-flowing powders from liquid lipophilic drugs or from water-insoluble drugs. The drugs are dissolved in suitable non-volatile solvents and mixed with carrier materials, such as microcrystalline or amorphous cellulose, to produce particles in the size range of 0.01 to 5 µm, and then coated with very fine silica powders. U.S. Pat. No. 5,780,062 to Frank et al. discloses formation of small particles of organic compounds by precipitation in an aqueous medium containing polymer/amphiphile complexes. U.S. Pat. No. 5,817,343 to Burke discloses a method for forming polymer/drug microparticles by forming a polymer solution/insoluble drug mixture; removing solvent from the mixture to form a hard matrix containing the drug particles in polymer; and micronizing the matrix by fragmenting (e.g., grinding, milling) the matrix below the glass-transition point of the polymer.

Sonication is another technique employed to micronize particles. For example, U.S. Pat. No. 4,384,975 to Fong et al. discloses the preparation of microspheres by solvent removal using sodium oleate as the emulsifier. Micronization of core material by milling or ultrasonic probe sonication of solid drug particles in polymer solution is disclosed. Tracy, *Biotechnol. Prog,* 14:108–15 (1998) discloses atomizing growth hormone in solution using an ultrasonic nozzle, freezing the dispersed droplets in a slurry of frozen ethanol, and then lyophilizing to remove the non-solvent and harden the droplets. The resulting hollow spheres are further micronized by ultrasonic probe treatment to fragment the spheres, which fragments are then encapsulated.

These methods are not desirable for micronizing certain types of agents, such as proteins. For example, exposure to high temperatures and/or an aqueous/organic solvent interface is known to be detrimental to protein stability leading to denaturation. It would be advantageous to provide dry, micronized particles of proteins, and a method of making such particles which substantially avoids or minimizes denaturation of the proteins. It would also be advantageous to provide dry micronized particles having a small, uniform size.

It is therefore an object of the present invention to provide a method of making dry particles of a protein or other agent, which process provides for the stabilization of the agent and produces very small particles of a uniform size, with minimal or no aggregation.

SUMMARY OF THE INVENTION

A process is provided for making dry, micronized particles of an agent. The method includes (a) dissolving a macromolecular material, preferably a polymer, in an effective amount of a solvent, to form a solution; (b) dissolving or dispersing the agent in the solution to form a mixture; (c) freezing the mixture; and (d) drying by vacuum (e.g., lyopholizing) the mixture to form solid particles of the agent dispersed in solid macromolecular material. Unlike prior methods of micronization, the micronization in this process occurs directly in a macromolecular matrix and hardening of the particles of agent by solvent removal takes place by lyophilization of the bulk matrix, which stabilizes the drug particles during hardening and prevents coalesence, thereby resulting in smaller final drug particles. Accordingly, the method is particularly preferred for protein agents, because proteins are much more stable in the dry state to temperature, chemical, and physical exposures, while the method minimizes the time the agent is exposed to an aqueous: organic interface. In one embodiment, the process is a distinct, pre-formulation step that subsequently is used in conjunction with a standard microencapsulation technique, typically following separation of the agent from the macromolecular matrix.

The process yields microparticles having a homogenous size distribution, preferably less than 2 μm, and more preferably less than 1 μm, in size. The microparticles have well defined, predictable properties, which is particularly critical in drug delivery applications.

BRIEF DESCRIPTION OF THE DRAWINGS

FIGS. 1*a* and 1*b* are graphs of cumulative release (micrograms FcOPG/mg, FIG. 1*a*; % total release, FIG. 1*b*) of FcOPG over time (hours) from polymeric microspheres prepared as described in examples 16–18.

FIGS. 2*a* and 2*b* are graphs of cumulative release (micrograms FcOPG/mg, FIG. 2*a*; % total release, FIG. ab) of FcOPG over time (hours) from polymeric microspheres prepared as described in examples 19–21.

FIGS. 3*a* and 3b are graphs of cumulative release (micrograms FcOPG/mg, FIG. 3*a*; % total release, FIG. 3*b*) of FcOPG over time (hours) from polymeric microspheres prepared as described in examples 22–24.

FIGS. 4*a* and 4*b* are graphs of cumulative release (micrograms FcOPG/mg, FIG. 4*a*; % total release, FIG. 4*b*) of FcOPG from polymeric microspheres prepared as described in examples 25, 28 and 30.

FIG. 5 is a graph of cumulative release of human growth hormone (hGH) over time (hours) from polymeric microspheres prepared as described in example 34.

FIG. 6 is a graph of serum hGH levels versus time (hours) following oral administration of hGH in microspheres prepared as described in example 32.

FIG. 7 is a graph of the percent release over time (hours) for lysosyme (closed square), carbonic anhydrase (closed circle), albumin (closed triangle), alcohol dehydrogenase (open square), and thyroglobulin (open thyroglobulin).

FIG. 8 is a graph of the precent release over time (hours) for lysosyme (closed square), carbonic anhydrase (closed circle), albumin (closed triangle), alcohol dehydrogenase (open square), and thyroglobulin (open thyroglobulin).

FIG. 9 is a graph of the precent of the original molecular weight over time (hours) for lysosyme (closed square), carbonic anhydrase (closed circle), albumin (closed triangle), alcohol dehydrogenase (open square), and thyroglobulin (open thyroglobulin).

FIG. 10 is a graph of the % of original mass over time (hours) for lysosyme (closed square), carbonic anhydrase (closed circle), albumin (closed triangle), alcohol dehydrogenase (open square), and thyroglobulin (open thyroglobulin) and control microspheres (-x-).

DETAILED DESCRIPTION OF THE INVENTION

An improved method has been developed for making dry, micronized particles of agents, e.g., drugs or other molecules.

I. Making Micronized, Freeze-Dried Particles

The process includes (a) dissolving a macromolecular material, preferably a polymer, in an effective amount of a solvent, to form a solution; (b) dissolving or dispersing the agent in the solution to form a mixture; (c) freezing the mixture; and (d) drying by vacuum the mixture to form solid particles of the agent dispersed in solid macromolecular material. The process is sometimes referred to herein as the "FLM process" or simply "FLM".

1. Preparing the Macromolecular Solution

The macromolecular material is combined with and dissolved in a solvent for the material using known mixing techniques.

2. Preparing the Mixture

The agent is added in its pure form or in a solution, directly to the macromolecular solution so as to form a well-dispersed mixture. As used herein, the term "mixture" refers to both emulsions and dispersions, unless otherwise indicated. Essentially any method known in the art for preparing mixtures can be used. Representative examples of such techniques include stirring, shaking, vortexing, and probe sonication. Surfactants may be used to stabilize the emulsion, preventing coalescence of primary emulsion droplets and maintaining the minimal final size of agent particle in the macromolecular matrix.

3. Freezing the Mixture

The mixture can be frozen using any technique known in the art. However, for proteins or other agents sensitive to the solvent, the mixture should be frozen rapidly after addition of the agent to the macromolecular solution. In one embodiment, a batch of the mixture is frozen by immersing a container of the mixture into a cooling apparatus, for example, containing liquid nitrogen. A closed cycle refrigeration system, such as the CRYOTIGER™ (IGC-APD Cryogenics Inc., Allentown, Pa.), also can be used, for example, to achieve temperatures as low as −203° C.

4. Drying the Frozen Mixture

The mixture should be dried rapidly and soon after freezing. The drying should remove all or substantially all of the solvent for the macromolecular material, as well as any solvent for the agent. Drying can be performed using any technique know in the art in which the mixture remains frozen.

In a preferred embodiment, the drying is performed under reduced pressure conditions, i.e. under vacuum. In other words, the mixture is lyophilized.

II. Encapsulating the Micronized Freeze-Dried Particles or Agent

In one embodiment, the micronization process described above is followed by additional processing in which the micronized particles of agent are separated from the macromolecular matrix and/or subject to additional microencapsulation, for example, using standard microencapsulation techniques.

1. Separation of Micronized Agent from Macromolecular Matrix

The matrix can be liquefied, either by dissolution in an appropriate solvent or by melting, and then separated from the solid particles of agent in the liquefied matrix material using standard separation techniques, such as filtration or centrifugation. If the matrix is dissolved, then the solvent must be a nonsolvent for the agent, which does not degrade the agent. If the matrix is melted, then the macromolecular material must have a melting temperature (Tm) lower than the Tm of the agent and be sufficiently low to avoid degradation of the agent.

2. Encapsulation Processes

The micronized particles of agent, with or without the matrix of macromolecular material, can serve as a core material in standard encapsulation processes. The core material typically is encapsulated in a polymeric material. Common microencapsulation techniques include interfacial polycondensation, spray drying, hot melt microencapsulation, and phase separation techniques (solvent removal and solvent evaporation).

(i) Interfacial Polycondensation

Interfacial polycondensation can be used to microencapsulate a core material in the following manner. One monomer and the core material are dissolved in a solvent. A second monomer is dissolved in a second solvent (typically aqueous) which is immiscible with the first. An emulsion is formed by suspending the first solution through stirring in the second solution. Once the emulsion is stabilized, an initiator is added to the aqueous phase causing interfacial polymerization at the interface of each droplet of emulsion.

(ii) Spray Drying

Spray drying is typically a process for preparing 1 to 10 µm-sized microspheres in which the core material to be encapsulated is dispersed or dissolved in a polymer solution (typically aqueous), the solution or dispersion is pumped through a micronizing nozzle driven by a flow of compressed gas, and the resulting aerosol is suspended in a heated cyclone of air, allowing the solvent to evaporate from the microdroplets. The solidified particles pass into a second chamber and are collected.

(iii) Hot Melt Microencapsulation

Hot melt microencapsulation is a method in which a core material is added to molten polymer. This mixture is suspended as molten droplets in a nonsolvent for the polymer (often oil-based) which has been heated approximately 10° C. above the melting point of the polymer. The emulsion is maintained through vigorous stirring while the nonsolvent bath is quickly cooled below the glass transition of the polymer, causing the molten droplets to solidify and entrap the core material. Microspheres produced by this technique typically range in size from 50 µm to 2 mm in diameter. This process generally requires the use of polymers with fairly low melting temperatures (e.g., less than 150° C.), glass transition temperatures above room temperature, and core materials which are thermo-stable.

(iv) Solvent Evaporation Microencapsulation

In solvent evaporation microencapsulation, the polymer is typically dissolved in a water-immiscible organic solvent and the material to be encapsulated is added to the polymer solution as a suspension or solution in organic solvent. An emulsion is formed by adding this suspension or solution to a beaker of vigorously stirring water (often containing a surface active agent to stabilize the emulsion). The organic solvent is evaporated while continuing to stir. Evaporation results in precipitation of the polymer, forming solid microcapsules containing core material.

(v) Phase Separation Microencapsulation

Phase separation microencapsulation is typically performed by dispersing the material to be encapsulated in a polymer solution by stirring. While continuing to uniformly suspend the material through stirring, a nonsolvent for the polymer is slowly added to the solution to decrease the polymer's solubility. The polymer either precipitates or phase separates into a polymer rich and a polymer poor phase, depending on the solubility of the polymer in the solvent and nonsolvent. Under proper conditions, the polymer in the polymer rich phase will migrate to the interface with the continuous phase, encapsulating the core material in a droplet with an outer polymer shell.

One embodiment of the process in described in U.S. Pat. No. 5,407,609 to Tice, et al., which discloses a phase separation microencapsulation process which reportedly proceeds very rapidly. In the method, a polymer is dissolved in a solvent, and then an agent to be encapsulated is dissolved or dispersed in that solvent. Then the mixture is combined with an excess of nonsolvent and is emulsified and stabilized, whereby the polymer solvent no longer is the continuous phase. Aggressive emulsification conditions are applied to produce microdroplets of the polymer solvent. The stable emulsion then is introduced into a large volume of nonsolvent to extract the polymer solvent and form microparticles. The size of the microparticles is determined by the size of the microdroplets of polymer solvent.

(vi) Phase Inversion Encapsulation a. Generally

Phase inversion is a term used to describe the physical phenomena by which a polymer dissolved in a continuous phase solvent system inverts into a solid macromolecular network in which the polymer is the continuous phase. This event can be induced through several means: removal of solvent (e.g., evaporation; also known as dry process), addition of another species, addition of a non-solvent or addition to a non-solvent (also known as wet process). In the wet process, the polymer solution can be poured or extruded into a non-solvent bath. The process proceeds in the following manner. The polymer solution undergoes a transition from a single phase homogeneous solution to an unstable two phase mixture polymer rich and polymer poor fractions. Micellar droplets of nonsolvent in the polymer rich phase serve as nucleation sites and become coated with polymer. At a critical concentration of polymer, the droplets precipitate from solution and solidify. Given favorable surface energy, viscosity and polymer concentrations, the micelles coalesce and precipitate to form a continuous polymer network.

Phase inversion phenomenon have been applied to produce macro and microporous polymer membranes and hollow fibers used in gas separation, ultrafiltration, ion exchange, and reverse osmosis. Structural integrity and morphological properties of these membranes are functions of polymer molecular weight, polymer concentration, solution viscosity, temperature and solubility parameters (of polymer, solvent and non-solvent). For wet process phase inversion, polymer viscosities must be greater than approximately 10,000 centipoise ("cP") to maintain membrane integrity; lower viscosity solutions may produce fragmented polymer particles as opposed to a continuous system. Furthermore, it is known that the quicker a solution is caused to precipitate, the finer is the dispersion of the precipitating phase.

A phase inversion process has been employed to produce polymer microcapsules. The microcapsules are prepared by dissolving a polymer in an organic solvent, forming droplets of the solution by forcing it through a spinneret or syringe needle, (the size of which droplets determines the size of the final microcapsule), and contacting the droplets with a nonsolvent for the polymer which is highly miscible with the polymer solvent, thereby causing rapid precipitation of the outer layer of the droplet. The microcapsules must be left in contact with the nonsolvent until substantially all of the solvent has been replaced with nonsolvent. This process requires formation of a droplet with dimensions established prior to contacting the nonsolvent.

Each of the methods described before require the formation of an emulsion or droplets prior to precipitation of the final microparticle. The method of producing microparticles without the requirement of forming an emulsion prior to precipitation. Under proper conditions, polymer solutions can be forced to phase invert into fragmented spherical polymer particles when added to appropriate nonsolvents. The process is simple to perform, is suitable with a number of polymeric systems (including many common degradable and non-degradable polymers typically employed as controlled release systems), produces extremely small microparticles (10 nm to 10 μm) and results in very high yields.

b. Phase Inversion Nanoencapsulation (PIN)

PIN is a nanoencapsulation technique which takes advantage of the immiscibility of dilute polymer solutions in select "non-solvents" in which the polymer solvent has good miscibility. The result is spontaneous formation of nanospheres (less than 1 μm) and microspheres (1–10 μm) within a narrow size range, depending on the concentration of the initial polymer solution, the molecular weight of the polymer, selection of the appropriate solvent-non-solvent pair and the ratio of solvent to non-solvent. Encapsulation efficiencies are typically 75–90% and recoveries are 70–90% and bioactivity is generally well-maintained for sensitive bioagents.

"Phase inversion" of polymer solutions under certain conditions can bring about the spontaneous formation of discreet microparticles. The process, called "phase inversion nanoencapsulation" or "PIN", differs from existing methods of encapsulation in that it is essentially a one-step process, is nearly instantaneous, and does not require emulsification of the solvent. Under proper conditions, low viscosity polymer solutions can be forced to phase invert into fragmented spherical polymer particles when added to appropriate non-solvents.

Phase inversion phenomenon has been applied to produce macro- and micro-porous polymer membranes and hollow fibers, the formation of which depends upon the mechanism of microphase separation. A prevalent theory of microphase separation is based upon the belief that "primary" particles form of about 50 nm diameter, as the initial precipitation event resulting from solvent removal. As the process continues, primary particles are believed to collide and coalesce forming "secondary" particles with dimensions of approximately 200 nm, which eventually join with other particles to form the polymer matrix. An alternative theory, "nucleation and growth", is based upon the notion that a polymer precipitates around a core micellar structure (in contrast to coalescence of primary particles).

The process results in a very uniform size distribution of small particles forming at lower polymer concentrations without coalescing supports the nucleation and growth theory, while not excluding coalescence at higher polymer concentrations (e.g., greater than 10% weight per volume) where larger particles and even aggregates can be formed. (Solvent would be extracted more slowly from larger particles, so that random collisions of the partially-solvated spheres would result in coalescence and, ultimately, formation of fibrous networks.) By adjusting polymer concentration, polymer molecular weight, viscosity, miscibility and solvent:nonsolvent volume ratios, the interfibrillar interconnections characteristic of membranes using phase inversion are avoided, with the result being that microparticles are spontaneously formed. These parameters are interrelated and the adjustment of one will influence the absolute value permitted for another.

In the preferred processing method, a mixture is formed of the agent to be encapsulated, a polymer and a solvent for the polymer. The agent to be encapsulated may be in liquid or solid form. It may be dissolved in the solvent or dispersed in the solvent. The agent thus may be contained in microdroplets dispersed in the solvent or may be dispersed as solid microparticles in the solvent. The phase inversion process thus can be used to encapsulate a wide variety of agents by including them in either micronized solid form or else emulsified liquid form in the polymer solution.

The loading range for the agent within the microparticles is between 0.01–80% (agent weight/polymer weight). When working with nanospheres, an optimal range is 0.1–5% (weight/weight).

The working molecular weight range for the polymer is on the order of 1 kDa–150,000 kDa, although the optimal range is 2 kDa–50 kDa. The working range of polymer concentration is 0.01–50% (weight/volume), depending primarily upon the molecular weight of the polymer and the resulting viscosity of the polymer solution. In general, the low molecular weight polymers permit usage of a higher concentration of polymer. The preferred concentration range will be on the order of 0.1%–10% (weight/volume), while the optimal polymer concentration typically will be below 5%. It has been found that polymer concentrations on the order of 1–5% are particularly useful.

The viscosity of the polymer solution preferably is less than 3.5 cP and more preferably less than 2 cP, although higher viscosities such as 4 or even 6 cP are possible depending upon adjustment of other parameters such as molecular weight. It will be appreciated by those of ordinary skill in the art that polymer concentration, polymer molecular weight and viscosity are interrelated, and that varying one will likely affect the others.

The nonsolvent, or extraction medium, is selected based upon its miscibility in the solvent. Thus, the solvent and nonsolvent are thought of as "pairs". The solubility parameter ($\delta$ (cal/cm$^3$)$^{1/2}$) is a useful indicator of the suitability of the solvent/nonsolvent pairs. The solubility parameter is an effective protector of the miscibility of two solvents and, generally, higher values indicate a more hydrophilic liquid while lower values represent a more hydrophobic liquid (e.g., $\delta_t$water=23.4(cal/cm$^3$)$^{1/2}$ whereas $\delta_t$hexane=7.3 (cal/cm$^3$)$^{1/2}$). Solvent/nonsolvent pairs are useful where 0|$\delta$ solvent–$\delta$ nonsolvent |<6 (cal/cm$^3$)$^{1/2}$. Although not wishing to be bound by any theory, an interpretation of this finding is that miscibility of the solvent and the nonsolvent is important for formation of precipitation nuclei which ultimately serve as foci for particle growth. If the polymer solution is totally immiscible in the nonsolvent, then solvent extraction does not occur and nanoparticles are not formed. An intermediate case would involve a solvent/nonsolvent pair with slight miscibility, in which the rate of solvent removal would not be quick enough to form discreet microparticles, resulting in aggregation of coalescence of the particles.

It was discovered that nanoparticles generated using "hydrophilic" solvent/nonsolvent pairs (e.g., a polymer dissolved in methylene chloride with ethanol as the nonsolvent) yielded approximately 100% smaller particles than when "hydrophobic" solvent/nonsolvent pairs were used (e.g., the same polymer dissolved in methylene chloride with hexane as the nonsolvent).

Similarly, it was discovered that the solvent:nonsolvent volume ratio was important in determining whether microparticles would be formed without particle aggregation or coalescence. A suitable working range for solvent:nonsolvent volume ratio is believed to be 1:40–1:1,000,000. An optimal working range for the volume ratios for solvent:nonsolvent is believed to be 1:50–1:200 (volume per volume). Ratios of less than approximately 1:40 resulted in particle coalescence, presumably due to incomplete solvent extraction or else a slower rate of solvent diffusion into the bulk nonsolvent phase.

It will be understood by those of ordinary skill in the art that the ranges given above are not absolute, but instead are interrelated. For example, although it is believed that the solvent:nonsolvent minimum volume ratio is on the order of 1:40, it is possible that microparticles still might be formed at lower ratios such as 1:30 if the polymer concentration is extremely low, the viscosity of the polymer solution is extremely low and the miscibility of the solvent and nonsolvent is high. Thus, the polymer is dissolved in an effective amount of solvent, and the mixture of agent, polymer and polymer solvent is introduced into an effective amount of a nonsolvent, to produce polymer concentrations, viscosities and solvent:nonsolvent volume ratios that cause the spontaneous and virtually instantaneous formation of microparticles.

A variety of polymers have been tested in the methods described herein, including polyesters such as poly(lactic acid), poly(lactide-co-glycolide) in molar ratios of 50:50 and 75:25; polycaprolactone; polyanhydrides such as poly(fumaric-co-sabacic) acid or P(FA:SA) in molar ratios of 20:80 and 50:50; poly(carboxyphenoxypropane-co-sebacic) acid or P(CPP:SA) in molar ratio of 20:80; and polystyrenes (PS). Poly(ortho)esters, blends and copolymers of these polymers can also be used, as well as other biodegradable polymers and non-biodegradable polymers such as ethylenevinyl acetate and polyacrylamides.

Nanospheres and microspheres in the range of 10 nm to 10 μm have been produced by these methods. Using initial polymer concentrations in the range of 1–2% (weight/volume) and solution viscosities of 1–2 cP, with a "good" solvent such as methylene chloride and a strong non-solvent such as petroleum ether or hexane, in an optimal 1:100 volume ratio, generates particles with sizes ranging from 100–500 μm. Under similar conditions, initial polymer concentrations of 2–5% (weight/volume) and solution viscosities of 2–3 cP typically produce particles with sizes of 500–3,000 nm. Using very low molecular weight polymers (less than 5 kDa), the viscosity of the initial solution may be low enough to enable the use of higher than 10% (weight/volume) initial polymer concentrations which generally result in microspheres with sizes ranging from 1–10 μm. In general, it is likely that concentrations of 15% (weight/volume) and solution viscosities greater than about 3.5 cP discreet microspheres will not form but, instead, will irreversibly coalesce into intricate, interconnecting fibrilar networks with micron thickness dimensions.

It is noted that only a limited number of microencapsulation techniques can produce particles smaller than 10 μm, and those techniques are associated with significant losses of polymer, the material to be encapsulated, or both. This is particularly problematic where the active agent is an expensive entity such as certain medical agents. These methods can result in product yields greater than 80% and encapsulation efficiencies as high as 100%, of nano- to micro-sized particles.

The methods described herein also can produce microparticles characterized by a homogeneous size distribution. Typical microencapsulation techniques produce heterogeneous size distributions ranging from 10 μm to mm sizes. Prior art methodologies attempt to control particle size by parameters, such as stirring rate, temperature, and polymer/suspension bath ratio. Such parameters, however, have not resulted in a significant narrowing of size distribution. The methods described herein can produce, for example, nanometer sized particles which are relatively monodisperse in size. By producing a microparticle that has a well defined and less variable size, the properties of the microparticle such as when used for release of a bioactive agent can be better controlled. Thus, the methods permit improvements in the preparation of sustained release formulations for administration to subjects.

The methods are also useful for controlling the size of the microspheres. This is particularly useful where the material to be encapsulated must first be dispersed in the solvent and where it would be undesirable to sonicate the material to be encapsulated. The mixture of the material to be encapsulated and the solvent (with dissolved polymer) can be frozen in liquid nitrogen and then lyophilized to disperse the material to be encapsulated in the polymer. The resulting mixture then can be redissolved in the solvent, and then dispersed by adding the mixture to the nonsolvent. This methodology was employed in connection with dispersing DNA, shown in the examples below.

In many cases, the methods can be carried out in less than five minutes in the entirety. Preparation time may take anywhere from one minute to several hours, depending on the solubility of the polymer and the chosen solvent, whether the agent will be dissolved or dispersed in the solvent and so on. Nonetheless, the actual encapsulation time typically is less than thirty seconds.

After formation of the microcapsules, they are collected by centrifugation, filtration, or other standard techniques. Filtering and drying may take several minutes to an hour depending on the quantity of material encapsulated and the methods used for drying the nonsolvent. The process in its entirety may be discontinuous or a continuous process.

Because the process does not require forming the solvent into an emulsion, it generally speaking may be regarded as a more gentle process than those that require emulsification. As a result, materials such as whole plasmids including genes under the control of promoters can be encapsulated without destruction of the DNA as a result of the emulsification process. Representative nucleotide molecules to be encapsulated include plasmids, vectors, external guide sequences for RNAase P, ribozymes and other sensitive oligonucleotides, the structure and function of which could be adversely affected by aggressive emulsification conditions and other parameters typical of certain of the prior art processes.

III. Composition of the Particles, Processing Materials

The micronized particles generally include solid particles of agent dispersed in a solid matrix of one or more macromolecules, typically a polymer.

1. Agent

Representative examples of the agent to be formed into particles include adhesives, gases, pesticides, herbicides, fragrances, antifoulants, dies, salts, oils, inks, cosmetics, catalysts, detergents, curing agents, flavors, foods, fuels, metals, paints, photographic agents, biocides, pigments, plasticizers, and propellants.

In a preferred embodiment, the agent is a bioactive agent. Representative examples of the bioactive agent include adrenergic agents; adrenocortical steroids; adrenocortical suppressants; aldosterone antagonists; amino acids; anabolics; analeptics; analgesics; anesthetics; anorectic; anti-acne agents; anti-adrenergics; anti-allergics; anti-amebics; anti-anemics; anti-anginals; anti-arthritics; anti-asthmatics; anti-atherosclerotics; antibacterials; anticholinergics; anticoagulants; anticonvulsants; antidepressants; antidiabetics; antidiarrheals; antidiuretics; anti-emetics; anti-epileptics; antifibrinolytics; antifungals; antihemorrhagics; antihistamines; antihyperlipidemias; antihypertensives; antihypotensives; anti-infectives; anti-inflammatories; antimicrobials; antimigraines; antimitotics; antimycotics, antinauseants, antineoplastics, antineutropenics, antiparasitics; antiproliferatives; antpsychotics; antirheumatics; antiseborrheics; antisecretories; antispasmodics; antithrombotics; anti-ulceratives; antivirals; appetite suppressants; blood glucose regulators; bone resorption inhibitors; bronchodilators; cardiovascular agents; cholinergics; depressants; diagnostic aids; diuretics; dopaminergic agents; estrogen receptor agonists; fibrinolytics; fluorescent agents; free oxygen radical scavengers; gastrointestinal motility effectors; glucocorticoids; hair growth stimulants; hemostatics; histamine H2 receptor antagonists; hormones; hypocholesterolemics; hypoglycemics; hypolipidemics; hypotensives; imaging agents; immunizing agents; immunomodulators; immunoregulators; immunostimulants; immunosuppressants; keratolytics; LHRH agonists; mood regulators; mucolytics; mydriatics; nasal decongestants; neuromuscular blocking agents; neuroprotective agents; NMDA antagonists; non-hormonal sterol derivatives; plasminogen activators; platelet activating factor antagonists; platelet aggregation inhibitors; psychotropics; radioactive agents; scabicides; sclerosing agents; sedatives; sedative-hypnotics; selective adenosine A1 antagonists; serotonin antagonists; serotonin inhibitors; serotonin receptor antagonists; steroids; thyroid hormones; thyroid inhibitors; thyromimetics; tranquilizers; amyotrophic lateral sclerosis agents; cerebral ischemia agents; Paget's disease agents; unstable angina agents; vasoconstrictors; vasodilators; wound healing agents; and xanthine oxidase inhibitors.

Bioactive agents include immunological agents such as allergens (e.g., cat dander, birch pollen, house dust, mite, and grass pollen) and antigens from pathogens such as viruses, bacteria, fungi and parasites. These antigens may be in the form of whole inactivated organisms, peptides, proteins, glycoproteins, carbohydrates, or combinations thereof. Specific examples of pharmacological or immunological agents that fall within the above-mentioned categories and that have been approved for human use may be found in the published literature.

2. Matrix Material/Encapsulation Material

The preferred matrix material is a polymer. The matrix material also can be used as the material for further encapsulation of the dried, micronized agent.

The polymer may be any suitable microencapsulation material including, but not limited to, nonbioerodable and bioerodable polymers. Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polymers of acrylic and methacrylic esters, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly (ethylene glycol), poly(ethylene oxide), poly(ethylene terephthalate), poly(vinyl alcohols), poly(vinyl acetate, poly vinyl chloride polystyrene and polyvinylpryrrolidone.

Examples of preferred non-biodegradable polymers include ethylene vinyl acetate, poly(meth) acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. The most preferred polymers are polyesters, polyanhydrides, polystyrenes and blends thereof.

Particularly preferred are bioadhesive polymers. A bioadhesive polymer is one that binds to mucosal epithelium under normal physiological conditions. Bioadhesion in the gastrointestinal tract proceeds in two stages: (1) viscoelastic deformation at the point of contact of the synthetic material into the mucus substrate, and (2) formation of bonds between the adhesive synthetic material and the mucus or the epithelial cells. In general, adhesion of polymers to tissues may be achieved by (i) physical or mechanical bonds, (ii) primary or covalent chemical bonds, and/or (iii) secondary chemical bonds (i.e., ionic). Physical or mechanical bonds can result from deposition and inclusion of the adhesive material in the crevices of the mucus or the folds of the mucosa. Secondary chemical bonds, contributing to bioadhesive properties, consist of dispersive interactions (i.e., Van der Waals interactions) and stronger specific interactions, which include hydrogen bonds. The hydrophilic functional groups primarily responsible for forming hydrogen bonds are the hydroxyl and the carboxylic groups. Numerous bioadhesive polymers are discussed in that application. Representative bioadhesive polymers of particular interest include bioerodible hydrogels described by Sawhney, et al., *Macromolecules,* 26:581–87 (1993), polyhyaluronic acids, casein, gelatin, glutin, polyanhydrides, polyacrylic acid, alginate, chitosan, poly(methyl methacrylates), poly(ethyl methacrylates), poly butylmethacrylate), poly (isobutylmethacrylate), poly(hexlmethacrylate), poly(isodecl methacrylate), poly(lauryl methacrylate), poly(phenyl methacrylate), poly (methyl acrylate), poly(isopropyl acrylate), poly(isobutyl acrylate), and poly(octadecl acrylate). Most preferred is poly(fumaric-co-sebacic)acid.

Polymers with enhanced bioadhesive properties can be provided wherein anhydride monomers or oligomers are incorporated into the polymer. The oligomer excipients can be blended or incorporated into a wide range of hydrophilic and hydrophobic polymers including proteins, polysaccharides and synthetic biocompatible polymers. Anhydride oligomers may be combined with metal oxide particles to improve bioadhesion even more than with the organic additives alone. Organic dyes because of their electronic charge and hydrophobicity/hydrophilicity can either increase or decrease the bioadhesive properties of polymers when incorporated into the polymers. The incorporation of oligomer compounds into a wide range of different polymers which are not normally bioadhesive dramatically increases their adherence to tissue surfaces such as mucosal membranes.

As used herein, the term "anhydride oligomer" refers to a diacid or polydiacids linked by anhydride bonds, and having carboxy end groups linked to a monoacid such as acetic acid by anhydride bonds. The anhydride oligomers have a molecular weight less than about 5000, typically between about 100 and 5000 daltons, or are defined as including between one to about 20 diacid units linked by anhydride bonds. In one embodiment, the diacids are those normally found in the Krebs glycolysis cycle. The anhydride oligomer compounds have high chemical reactivity.

The oligomers can be formed in a reflux reaction of the diacid with excess acetic anhydride. The excess acetic anhydride is evaporated under vacuum, and the resulting oligomer, which is a mixture of species which include between about one to twenty diacid units linked by anhydride bonds, is purified by recrystallizing, for example from toluene or other organic solvents. The oligomer is collected by filtration, and washed, for example, in ethers. The reaction produces anhydride oligomers of mono and poly acids with terminal carboxylic acid groups linked to each other by anhydride linkages.

The anhydride oligomer is hydrolytically labile. As analyzed by gel permeation chromatography, the molecular weight may be, for example, on the order of 200–400 for fumaric acid oligomer (FAO) and 2000–4000 for sebacic acid oligomer (SAPP). The anhydride bonds can be detected by Fourier transform infrared spectroscopy by the characteristic double peak at 1750 $cm^{-1}$ and 1820 $cm^{-1}$, with a corresponding disappearance of the carboxylic acid peak normally at 1700 $cm^{-1}$.

In one embodiment, the oligomers may be made from diacids described for example in U.S. Pat. No. 4,757,128 to Domb et al., U.S. Pat. No. 4,997,904 to Domb, and U.S. Pat. No. 5,175,235 to Domb et al., the disclosures of which are incorporated herein by reference. For example, monomers such as sebacic acid, bis(p-carboxy-phenoxy)propane, isophathalic acid, fumaric acid, maleic acid, adipic acid or dodecanedioic acid may be used.

Organic dyes, because of their electronic charge and hydrophilicity/ hydrophobicity, may alter the bioadhesive properties of a variety of polymers when incorporated into the polymer matrix or bound to the surface of the polymer. A partial listing of dyes that affect bioadhesive properties include, but are not limited to: acid fuchsin, alcian blue, alizarin red s, auramine o, azure a and b, Bismarck brown y, brilliant cresyl blue ald, brilliant green, carmine, cibacron blue 3GA, congo red, cresyl violet acetate, crystal violet, eosin b, eosin y, erythrosin b, fast green fcf, giemsa, hematoylin, indigo carmine, Janus green b, Jenner's stain, malachite green oxalate, methyl blue, methylene blue, methyl green, methyl violet 2b, neutral red, Nile blue a, orange II, orange G, orcein, paraosaniline chloride, phloxine b, pyronin b and y, reactive blue 4 and 72, reactive brown 10, reactive green 5 and 19, reactive red 120, reactive yellow 2, 3, 13 and 86, rose bengal, safranin o, Sudan III and IV, Sudan black B and toluidine blue.

3. Solvent for the Agent

In a preferred embodiment, the solvent is biocompatible and aqueous.

4. Solvent for the Matrix Material

The solvent is any suitable solvent for dissolving the polymer. Typically the solvent will be a common organic solvent such as a halogenated aliphatic hydrocarbon such as methylene chloride, chloroform and the like; an alcohol; an aromatic hydrocarbon such as toluene; a halogenated aromatic hydrocarbon; an ether such as methyl t-butyl; a cyclic ether such as tetrahydrofuran; ethyl acetate; diethylcarbonate; acetone; or cyclohexane. The solvents may be used alone or in combination. The solvent chosen must be capable of dissolving the polymer, and it is desirable that the solvent be inert with respect to the agent being encapsulated and with respect to the polymer.

IV. Applications for the Micronized Particles

In a preferred embodiment, the agent is a bioactive agent and the particles are administered to a patient in need thereof. The particles can be administered by themselves, e.g., as a dry powder, or incorporated into a physiologically acceptable carrier, such as saline.

The micronized particles also can be microencapsulated for delivery, with or without the macromolecular matrix formed in the micronization process.

The present invention will be further understood with reference to the following non-limiting examples.

EXAMPLE 1

Stabilization of Protein in Initial Emulsion in FLM Matrix with Lecithin and SPAN™ 85

This experiment investigated the factors that were important in obtaining a small (less than 5 μm) primary emulsion size during the first step of FLM, prior to freezing. As a test protein, bovine serum albumin (BSA), covalently labeled with the fluorescent label, fluroescein isothiocyanate (FITC) was used as a 10 mg/ml solution in 0.2 M sodium phosphate, pH 7.6. In some cases, the protein solution was diluted 1:1 (final BSA concentration: 5 mg/ml) with 10% mannitol (w/v) to test the effect of the mannitol on stabilizing the emulsion.

The polymer solution used was poly-lactide-co-glycolide (PLGA) in 50:50 molar ratio (MW=12 kDA, RG 502H, Boehringer Ingelheim) dissolved in methylene chloride ("MC") at a concentration of 3 or 6% (w/v). Additionally two surfactants were tested for their ability to stabilize and reduce the primary emulsion size: SPAN™ 85 as a 1% (v/v) solution in methylene chloride ("MCS85") and Lecithin as a 1% (w/v) solution in methylene chloride ("MCL"). These two detergent solutions in methylene chloride were used as solvents for the PLGA polymer.

Materials and Methods

A typical experiment consisted of adding 0.05 ml of 10 mg/ml BSA solution to 1.0 ml of 3% PLGA (w/v) in methylene chloride either with or without added surfactant. The water/oil mixture was vortexed for 30 s at the maximum amplitude of a "Supermixer 2" (Labcraft Industries). The emulsion droplet size was immediately examined with a fluorescent light microscope and the size judged using a reticle. The results of each test is shown in Table 1.

TABLE 1

Formulation and Emulsion Droplet Size

| Test | Polymer | Lecithin | SPAN™ 85 | Water:Oil Ratio | Mannitol | Emulsion Droplet Size (μm) |
|---|---|---|---|---|---|---|
| 1 | No | No | No | 1:20 | No | 5–30 |
| 2 | No | Yes | No | 1:20 | No | 5–30 |
| 3 | No | Yes | No | 1:2 | No | 5–30 |
| 4 | 3% PLGA | Yes | No | 1:20 | No | <1–5 |
| 5 | 3% PLGA | Yes | No | 1:2 | No | 10–100 |
| 6 | 3% PLGA | No | No | 1:20 | No | <5 |
| 7 | 3% PLGA | Yes | No | 1:20 | Yes | <5 |
| 8 | No | No | Yes | 1:20 | No | 1–5 |
| 9 | 3% PLGA | No | Yes | 1:20 | No | <1 |
| 10 | 3% PLGA | No | Yes | 1:20 | Yes | <1 |

EXAMPLE 2

FLM and PIN of Insulin

FLM Procedure

In this formulation, 1.176 g PLGA 50:50 RG 502 H was dissolved in 28 ml of methylene chloride, yielding a 3.09% w/v solution of the base polymer. Then, 0.1198 g of $Fe_3O_4$ (5.2% w/w of the total) was blended, and 0.5880 g of fumaric acid prepolymer ("FAO") was dissolved in 10 ml of acetone and blended at a loading of 25.6% w/w of the total. Bovine zinc insulin (USB Amersham) was dispersed into the mixture by adding 36.2 ml of 13.6 mg/ml zinc insulin in 0.01 N HCl to 38 ml of the polymer solution. The mixture was vigorously hand-shaken for 1 min., vortexed for 30 s, and then probe sonicated for 1 min. at 28% amplitude with a microtip. The emulsion was immediately frozen in liquid nitrogen for 5 min. and lyophilized for 46 hours. The resulting composition of the dry solids is shown in Table 2.

TABLE 2

Composition Resulting from FLM

| Component | % of Total (w/w) |
|---|---|
| PLGA RG 502 H | 51.2% |
| Zinc Insulin | 18.0% |
| FAO | 25.6% |
| $Fe_3O_4$ | 5.2% |
| Total | 100.0% |

Phase Inversion Nanoencapsulation

The dry solids from the FLM procedure were resuspended in 58.8 ml of methylene chloride so that the PLGA concentration was 2% w/v. The suspension was continuously bath sonicated before phase inversion processing. A single batch consisted of pouring 20 ml of polymer solution into 1.0 L of petroleum ether in a 1 L beaker (solvent to non-solvent ratio=1:50). After 30 s, particles were collected by vacuum filtration with analytical filter paper, air-dried for 10 min. at room temperature and scraped from the filter paper. Large clumps were broken up by "dicing" with a razor blade. The final powder was additionally treated with a water-cooled micromill for 1 min. to break up clumps. Three batches were prepared and the resulting particles were pooled, collected, and weighed to give 1.5972 g of microspheres, a yield of 69.5%.

Scanning Electron Microscopy

The microspheres were examined by SEM and found to consist of small discrete particles having a very narrow size distribution of less than 0.1 to 0.5 μm, with an average size of about 0.2 μm. The microspheres were spherical with smooth, non-porous surfaces.

Insulin Extraction and In Vitro Release Studies

Nominally approximately 10 mg aliquots of microspheres in triplicate were dissolved in 0.5 ml of methylene chloride and extracted with 1.0 ml of 0.005N HCl. Protein was determined using the Pierce BCA assay. The loading of insulin was determined to be 19.2%±0.1 % (w/w), compared to the nominal loading of 18% w/w, for an efficiency of 106.6%.

Triplicate approximately 10 mg aliquots were used to determine release in vitro by incubating microspheres in successive 1.0 ml volumes of fresh, phosphate-buffered saline, pH 7.2 ("PBS") at 37° C. Protein was determined in incubation fluids from 1, 2.25, 3.25, 4.25, 6.25, and 24 hr time points, using the Pierce BCA assay. To facilitate solubility of insulin in all incubation fluids, 10 μL of concentrated HCl was added after the incubation was complete. The final pH of the acidified fluids was less than 3. The Pierce assay states that 0.1N HCl is not an interference. The release results are shown in Table 3, with standard error ("S.E."). Nearly 15% of the insulin loading was released after the first hour of incubation and 92% after 3.25 hrs. At the end of 24 hours, the final extraction accounted for the remaining 1 % of the insulin.

TABLE 3

Cumulative Release In Vitro as a Function of Time

| Time (hrs) | % Cumulative Release | S.E. |
|---|---|---|
| 1.0 | 15.0 | 1.0 |
| 2.25 | 71.0 | 7.0 |
| 3.25 | 92.0 | 1.0 |
| 4.25 | 96.0 | 0 |
| 6.25 | 97.0 | 0 |
| 24.0 | 99.0 | 0 |

Particle Size Analysis

Approximately 100 mg of microspheres were resuspended in 20 ml of 0.9% NaCl, 0.01% TWEEN™ 20 (w/v), and 0.01% TWEEN™ 80 (w/v) and then dispersed by 2×30 s alternating cycles of vortexing and bath sonication. The suspension was introduced into an LS 230 Coulter laser particle size analyzer and statistics for volume and number distribution were determined.

HPLC Analysis

HPLC was conducted using a Waters 2690 Separations Module with a Waters 996 Photodiode Array (PDA) detector. The insulin assay was a modified version of the U.S.P. protocol, running an isocratic mobile phase of 75% sodium sulphate buffer (pH 2.7) and 25% acetonitrile. The column used was a NovaPak C18 3.9×150 mm reversed phase column. Samples were extracted/solubilized in 0.01N HCl and filtered with a 0.2 μm syringe filter. Peaks were analyzed using Millenium chromatography software. The results showed a single peak with retention times of 2.927 and 3.197 min. in duplicate runs. The area of the peak was 163240 μV*sec (run 1) and 169000 μV*sec (run 2).

EXAMPLE 3

FLM and PIN of Insulin

FLM Procedure

In this formulation, 1.176 g PLGA 50:50 RG 502 H was dissolved in 28 ml of methylene chloride, yielding a 3.79% w/v solution of the base polymer. Then, 0.1198 g of $Fe_3O_4$ (5.2% w/w of the total) was blended. Next, 0.5880 g of FAO was dissolved in 3 ml of acetone and blended at a loading of 25.6% w/w of the total. Bovine zinc insulin (GIBCO) was then dispersed into the mixture by adding 56.1 ml of 7.36 mg/ml zinc insulin in 0.005 N HCl to 31 ml of polymer solution. The mixture was vortexed for 20 s and probe sonicated for 1 min. at 38% amplitude with a microtip. The emulsion was immediately frozen in liquid nitrogen for 5 min. and lyophilized for 69 hours. The resulting composition of the dry solids is shown in Table 4.

TABLE 4

Composition Resulting from FLM

| Component | % of Total (w/w) |
|---|---|
| PLGA RG 502 H | 51.2% |
| Zinc Insulin | 18.0% |
| FAO | 25.6% |
| $Fe_3O_4$ | 5.2% |
| Total | 100.0% |

Phase Inversion Nanoencapsulation

The resulting dry solids were resuspended in 43.0 ml of methylene chloride so that the PLGA concentration was 2% w/v. The suspension was continuously bath sonicated before phase inversion processing. A single batch consisted of pouring 21.5 ml of polymer solution into 1.1 L of petroleum ether in a 1 L beaker (solvent to non-solvent ratio=1:50). After 30 s, particles were collected by vacuum filtration with analytical filter paper, air-dried for 10 min. at room temperature and scraped from the filter paper, with large clumps "diced" as in Example 1. Two batches were prepared and the resulting particles were pooled, collected, and weighed to give 1.37 g of microspheres, a yield of 81.5%. Some of the material losses occurred during lyophilization following the micronization step, and were not included in the yield calculation from PIN.

Scanning Electron Microscopy

Microspheres were examined by SEM and were found to consist of a mixture of small discrete particles and plates. The particles were a mixture of spherical and irregular-shaped morphologies. Many aggregates and plate-like aggregates were observed. Particles were between 0.001 and 3 μm in size, with an average size of about 0.5 μm. All morphologies had smooth, non-porous surfaces.

Insulin Extraction and In Vitro Release Studies

Aliquots were prepared as in Example 2. The loading of insulin was determined to be 16.4%±1.9% (w/w), compared to the nominal loading of 18% w/w, for an efficiency of 91%.

Triplicate approximately 10 mg aliquots were used to determine release in vitro by incubating microspheres in successive 1.0 ml volumes of PBS, pH 7.2 at 37° C. Protein was determined in incubation fluids from 1, 2, 3, 4, and 5 hr time points, using the Pierce BCA assay. To facilitate solubility of insulin in all incubation fluids, 5 μL of concentrated HCl was added after the incubation was complete. The final pH of the acidified fluids was less than 3. The release results are shown in Table 6. Nearly 16% of the insulin loading was released after the first hour of incubation and 65% after 3 hrs. At the end of 5 hours, the final extraction accounted for the remaining 28.2% of the insulin. The results are shown in Table 5.

TABLE 5

Cumulative Release In Vitro as a Function of Time

| Time (hrs) | % Cumulative Release | S.E. |
|---|---|---|
| 1.0 | 16.2 | 9.2 |
| 2.0 | 50.1 | 12.9 |
| 3.0 | 64.5 | 18.6 |
| 4.0 | 69.5 | 21.3 |
| 5.0 | 71.1 | 21.9 |

EXAMPLE 4

FLM and PIN of Insulin

FLM Procedure

For this formulation, 1.7627 g PLGA 50:50 RG 502 H was dissolved in 42 ml of methylene chloride, yielding a 3.83% w/v solution of the base polymer. In this run, 0.1802 g of $Fe_3O_4$ (5.5% w/w of the total) was blended, and 0.8814 g of FAO dissolved in 4 ml of acetone was blended at a loading of 26.8% w/w of the total. Bovine zinc insulin (GIBCO) was dispersed into the mixture by adding 63.9 ml of 7.36 mg/ml zinc insulin in 0.005 N HCl to 46 ml of polymer solution. The mixture was emulsified, frozen, and lyophilized as in Example 3. The resulting composition of the dry solids is shown in Table 6.

TABLE 6

Composition Resulting from FLM

| Component | % of Total (w/w) |
|---|---|
| PLGA RG 502 H | 53.5% |
| Zinc Insulin | 14.3% |
| FAO | 26.8% |
| $Fe_3O_4$ | 5.5% |
| Total | 100.0% |

Phase Inversion Nanoencapsulation

The resulting dry solids were resuspended in 61.0 ml of methylene chloride to a PLGA concentration of 2% w/v. The suspension was continuously bath sonicated before phase inversion processing. A single batch consisted of pouring 20 ml of polymer solution into 1.0 L of petroleum ether in a 1 L beaker (solvent to non-solvent ratio=1:50). After 30 s, particles were collected by vacuum filtration with analytical filter paper, air-dried for 10 min. at room temperature, and scraped from the filter paper. Large clumps were diced. Three batches were prepared and the resulting particles were pooled, collected, and weighed to give 6.853 g of microspheres, a yield of 74.1%.

Scanning Electron Microscopy

Microspheres examined by SEM were found to consist of small discrete particles, generally less than 1 µm in size, with an average size of about 0.2 µm. Morphologies were a mix of spherical and irregular shapes with smooth, non-porous surfaces.

Insulin Extraction and In Vitro Release Studies

Nominally approximately 10 mg aliquots of microspheres in triplicate were dissolved in 0.5 ml of methylene chloride and extracted with 1.0 ml of 0.005N HCl. Protein was determined using the Pierce BCA assay. The loading of insulin was determined to be 16.4%±0.5% (w/w), compared to the nominal loading of 14.3% w/w, for an efficiency of 114.3%.

Triplicate approximately 10 mg aliquots were used to determine release in vitro by incubating microspheres in successive 1.0 ml volumes of fresh PBS, pH 7.2 at 37° C. Protein was determined in incubation fluids from 1, 2, 3, 4, and 5 hr time points. To facilitate solubility of insulin in all incubation fluids,10 µL of concentrated HCl was added after the incubation was complete. The final pH of the acidified fluids was less than 3. The release results are shown in Table 7. Nearly 17% of the insulin loading was released after the first hour of incubation, and 34% after 3 hrs. At the end of 5 hrs, the final extraction accounted for the remaining 65.1% of the insulin.

TABLE 7

Cumulative Release In Vitro as a Function of Time

| Time (hrs) | % Cumulative Release | S.E. |
|---|---|---|
| 1.0 | 16.7 | 1.9 |
| 2.0 | 28.7 | 6.8 |
| 3.0 | 31.5 | 8.1 |
| 4.0 | 32.6 | 8.3 |
| 5.0 | 33.9 | 7.9 |

EXAMPLE 5

FLM and PIN of Insulin

FLM Procedure

For this formulation, 1.5 g PLGA 50:50 RG 502 H was dissolved in 20 ml of acetone, yielding a 1.6% w/v solution of the base polymer. In this run, 0.30 g of $Fe_3O_4$ (10.5% w/w of the total) was blended, and 0.75 g of FAO dissolved in 4 ml of acetone was blended at a loading of 26.3% w/w of the total. Bovine zinc insulin (USB Amersham) was dispersed into the mixture by adding 23 ml of 13.6 mg/ml zinc insulin in 0.01 N HCl to 95 ml of polymer solution. The mixture was vigorously hand-shaken for 0.5 min., vortexed for 30 s, probe sonicated for 1 min. at 28% amplitude with a microtip, and homogenized with a Virtishear roto-stator head at 70% amplitude for 1 min. using the fluted 500 ml homogenization vessel. The emulsion was immediately frozen in liquid nitrogen for 5 min. and lyophilized for 73 hrs. The resulting composition of the dry solids is shown in Table 8.

TABLE 8

Composition Resulting from FLM

| Component | % of Total (w/w) |
|---|---|
| PLGA RG 502 H | 52.6% |
| Zinc Insulin | 10.53% |
| FAO | 26.3% |
| $Fe_3O_4$ | 10.5% |
| Total | 100.0% |

Phase Inversion Nanoencapsulation

The resulting dry solids were resuspended in 75 ml of methylene chloride so that the PLGA concentration was 2% w/v. The suspension was continuously bath sonicated before phase inversion processing. A single batch consisted of pouring 20 ml of polymer solution into 1.0 L of petroleum ether in a 1 L beaker (solvent to non-solvent ratio=1:50) or pouring 15 ml of polymer solution into 750 ml of petroleum ether. After 30 s, particles were collected by vacuum filtration with analytical filter paper, air-dried for 10 min. at room temperature, scraped from the filter paper, and large clumps diced. The final powder was additionally treated with a water-cooled micromill for 1 min. to break up clumps. Four batches were prepared (three at 20 ml polymer:1 L non-solvent and one at 15 ml polymer:750 ml non-solvent) and the resulting particles were pooled. This resulted in 1.5245 g of microspheres collected, for a yield of 53.5%.

Scanning Electron Microscopy

Microspheres were examined by SEM and were found to consist of some small discrete particles, in a very narrow size distribution of less than 0.01 to 0.02 µm, with an average size of about 0.02 µm. Most particles were in clumps, but still discrete, with smooth surface morphologies. Many plate-like crystals in the size range of 1 to 5 µm also were observed.

Insulin Extraction and In Vitro Release Studies

Nominally approximately 10 mg aliquots of microspheres in triplicate were dissolved in 0.5 ml of methylene chloride and extracted with 1.0 ml of 0.005 N HCl. Protein was determined using the Pierce BCA assay. The loading of insulin was determined to be 14.2%±1.3% (w/w), compared to the nominal loading of 10.5% w/w, for an efficiency of 135.2%.

Triplicate approximately 10 mg aliquots were used to determine release in vitro by incubating microspheres in successive 1.0 ml volumes of fresh PBS, pH 7.2 at 37° C. Protein was determined in incubation fluids from 1, 2, 3, 4, 5, 7, and 24 hr time points. To facilitate solubility of insulin in all incubation fluids,10 µL of concentrated HCl was added after the incubation was complete. The final pH of the acidified fluids was less than 3. The release results are shown in Table 9. Nearly 3% of the insulin loading was released after the first hour of incubation and 98% after 3 hrs. At the end of 24 hrs, the final extraction accounted for the remaining 0% of the insulin.

TABLE 9

Cumulative Release In Vitro as a Function of Time

| Time (hrs) | % Cumulative Release | S.E. |
|---|---|---|
| 1.0 | 3.0 | 1.0 |
| 2.0 | 89.0 | 1.0 |
| 3.0 | 98.0 | 0 |
| 4.0 | 99.0 | 0 |
| 5.0 | 99.0 | 0 |
| 24.0 | 100.0 | 0 |

EXAMPLE 6

FLM and PIN of Insulin

FLM Procedure

For this formulation, 1.5 g PLGA 50:50 RG 502 H was dissolved in 75 ml of methylene chloride, yielding a 1.6% w/v solution of the base polymer. In this run, 0.30 g of $Fe_3O_4$ (8.33% w/w of the total) was blended, and 1.5 g of FAO dissolved in 20 ml of acetone was blended at a loading of 41.66% w/w of the total. Bovine zinc insulin (USB Amersham) was dispersed into the mixture by adding 23 ml of 13.6 mg/ml zinc insulin in 0.01 N HCl to 95 ml of polymer solution. The mixture was emulsified, frozen, and lyophilized as in Example 5. The resulting composition of the dry solids is shown in Table 10.

TABLE 10

Composition Resulting from FLM

| Component | % of Total (w/w) |
|---|---|
| PLGA RG 502 H | 41.66% |
| Zinc Insulin | 8.33% |
| FAO | 41.66% |
| $Fe_3O_4$ | 8.33% |
| Total | 100.0% |

Phase Inversion Nanoencapsulation

The resulting dry solids were resuspended, encapsulated, and analyzed as in Example 5, with 1.262 g of microspheres collected. The yield was 35.1%.

Scanning Electron Microscopy

Microspheres were examined by SEM and were found to consist of some small discrete particles, in a very narrow size distribution of less than 0.01 to 0.03 µm, with an average size of about 0.03 µm. Most particles were in clumps, but still discrete, with smooth surface morphologies.

Insulin Extraction and In Vitro Release Studies

Aliquots were prepared as in Example 5. The loading of insulin was determined to be 13.2%±0.7% (w/w) compared to the nominal loading of 8.33% w/w, for an efficiency of 158.46%.

Protein was determined as in Example 5. The release results are shown in Table 11. Nearly 3% of the insulin loading was released after the first hour of incubation and 80% after 3 hrs. At the end of 24 hrs, the final extraction accounted for the remaining 1% of the insulin.

TABLE 11

Cumulative Release In Vitro as a Function of Time

| Time (hrs) | % Cumulative Release | S.E. |
|---|---|---|
| 1.0 | 3.0 | 1.0 |
| 2.0 | 72.0 | 0.0 |
| 3.0 | 80.0 | 2.0 |
| 4.0 | 82.0 | 2.0 |
| 5.0 | 83.0 | 2.0 |
| 7.0 | 85.0 | 2.0 |
| 24.0 | 99.0 | 1.0 |

EXAMPLE 7

FLM and PIN of Insulin—Sixth Experiment

FLM Procedure

For this formulation, 1.5 g PLGA 50:50 RG 502 H was dissolved in 75 ml of methylene chloride, yielding a 1.6% w/v solution of the base polymer. In this run, 0.30 g of $Fe_3O_4$ (8.33% w/w of the total) was blended, and 1.5 g of FAO dissolved in 20 ml of acetone was blended at a loading of 41.66% w/w of the total. Bovine zinc insulin (USB Amersham) was dispersed into the mixture by adding 23 ml of 13.6 mg/ml zinc insulin in 0.01 N HCl, with 10 ml of 10% zinc sulfate added dropwise, to 95 ml of polymer solution. The mixture was vigorously hand-shaken for 0.5 min. and probe sonicated for 1.5 min at 35% amplitude with a microtip. The emulsion was immediately frozen in liquid nitrogen for 5 min. and lyophilized for 48 hrs. The resulting composition of the dry solids is shown in Table 12.

TABLE 12

Composition Resulting from FLM

| Component | % of Total (w/w) |
|---|---|
| PLGA RG 502 H | 41.66% |
| Zinc Insulin | 8.33% |
| FAO | 41.66% |
| $Fe_3O_4$ | 8.33% |
| Total | 100.0% |

Phase Inversion Nanoencapsulation

The resulting dry solids were resuspended, encapsulated, and analyzed as in Example 5, with 1.5875 g of microspheres collected. The yield was 44.1%. There were high losses to the filter paper; as large amounts of the material stuck to the filter paper and could not be removed.

Scanning Electron Microscopy

Microspheres were examined by SEM and were found to consist of some small discrete particles, in a very narrow size distribution of less than 0.01 to 0.03 µm, with an average size of about 0.03 µm. Most particles were in clumps, but were discrete with smooth surface morphologies. Small spheres, unencapsulated insulin crystals, and small plates about 1 to 8 μm in size also were observed.

Insulin Extraction and In Vitro Release Studies

Aliquots were prepared as in Example 5. The loading of insulin was determined to be 15.6%±1.9% (w/w), compared to the nominal loading of 8.33% w/w for an efficiency of 187.3%.

Protein was determined as in Example 5. The release results are shown in Table 13. Nearly 1% of the insulin loading was released after the first hour of incubation and 90% after 3 hrs. At the end of 24 hrs, the final extraction accounted for the remaining 0% of the insulin.

TABLE 13

Cumulative Release In Vitro as a Function of Time

| Time (hrs) | % Cumulative Release | S.E. |
|---|---|---|
| 1.0 | 1.0 | 0.0 |
| 2.0 | 78.0 | 3.0 |
| 3.0 | 90.0 | 3.0 |
| 4.0 | 90.0 | 3.0 |
| 5.0 | 93.0 | 2.0 |
| 7.0 | 93.0 | 2.0 |
| 24.0 | 100.0 | 0.0 |

EXAMPLE 7

FLM and PIN of Vancomycin

FLM Procedure

In this formulation, 1.0 g PLGA 50:50 RG 502 H was dissolved in 20 ml of methylene chloride, yielding a 2.86% w/v solution of the base polymer. Then, 0.20 g of $Fe_3O_4$ (8.16% w/w of the total) was blended, and 1.0 g of FAO was dissolved in 15 ml of acetone and blended at a loading of 40.82% w/w of the total. Vancomycin HCl (Sigma) was dispersed into the mixture by adding 5 ml of 5% Vancomycin HCl in distilled water to 35 ml of polymer solution. The mixture was vigorously hand-shaken for 0.5 min. and probe sonicated for 1.0 min. at 36% amplitude with a microtip. The emulsion was immediately frozen in liquid nitrogen for 5 min. and lyophilized for 64 hours. The resulting composition of the dry solids is shown in Table 14.

TABLE 14

Composition Resulting from FLM

| Component | % of Total (w/w) |
|---|---|
| PLGA RG 502 H | 40.82% |
| Vancomycin HCl | 10.20% |
| FAO | 40.82% |
| $Fe_3O_4$ | 8.16% |
| Total | 100.0% |

Phase Inversion Nanoencapsulation

The resulting dry solids were resuspended, encapsulated, and analyzed as in Example 5, with 1.4797 g of microspheres collected. The yield was 60.4%.

Scanning Electron Microscopy

Microspheres were examined by SEM and were found to consist of some small discrete particles, in a very narrow size distribution of less than 0.1 to 3 μm with an average size of about 1 μm. Unencapsulated vancomycin was observed. Particles were irregularly shaped with smooth surface morphology.

EXAMPLE 8

FLM and PIN of Vancomycin

FLM Procedure

In this formulation, 1.0 g PLGA 50:50 RG 502 H was dissolved in 20 ml of methylene chloride, yielding a 3.33% w/v solution of the base polymer. Then, 0.20 g of $Fe_3O_4$ (8.47% w/w of the total) was blended, and 1.0 g of FAO was dissolved in 10 ml of acetone and blended at a loading of 42.38% w/w of the total. Vancomycin HCl (Sigma) was dispersed into the mixture by adding 0.7 ml of 227.3 mg/ml Vancomycin HCl in distilled water to 30 ml of polymer solution. The mixture was emulsified, frozen, and lyophilized as in Example 7. The resulting composition of the dry solids is shown in Table 15.

TABLE 15

Composition Resulting from FLM

| Component | % of Total (w/w) |
|---|---|
| PLGA RG 502 H | 42.38% |
| Vancomycin HCl | 6.78% |
| FAO | 42.38% |
| $Fe_3O_4$ | 8.47% |
| Total | 100.0% |

Phase Inversion Nanoencapsulation

The resulting dry solids were resuspended, encapsulated, and analyzed as in Example 5, with 1.3821 g of microspheres collected. The yield was 58.9%.

EXAMPLE 9

FLM and PIN of Vancomycin

FLM Procedure

In this formulation, 1.0 g PLGA 50:50 RG 502 H was dissolved in 20 ml of methylene chloride, yielding a 3.33% w/v solution of the base polymer. Then, 0.20 g of $Fe_3O_4$ (8.47% w/w of the total) was blended, and 1.0 g of FAO was dissolved in 10 ml of acetone and blended at a loading of 43.67% w/w of the total. Vancomycin HCl (Sigma) was dispersed into the mixture by adding 0.4 ml of 227.3 mg/ml Vancomycin HCl in distilled water to 30 ml of polymer solution. The mixture was emulsified, frozen, and lyophilized as in Example 7. The resulting composition of the dry solids is shown in Table 16.

TABLE 16

Composition Resulting from FLM

| Component | % of Total (w/w) |
|---|---|
| PLGA RG 502 H | 42.38% |
| Vancomycin HCl | 3.93% |
| FAO | 43.67% |
| $Fe_3O_4$ | 8.73% |
| Total | 100.0% |

Phase Inversion Nanoencapsulation

The resulting dry solids were resuspended in 50 ml of methylene chloride so that the PLGA concentration was 2% w/v. The suspension was continuously bath sonicated before phase inversion processing. A single batch consisted of pouring 20 ml of polymer solution into 1.0 L of petroleum ether in a 1 L beaker (solvent to non-solvent ratio=1:50) or pouring 10 ml of polymer solution into 500 ml of petroleum ether. After 30 s, particles were collected by vacuum filtration with analytical filter paper, air-dried for 10 min. at room temperature, and scraped from the filter paper. Large clumps were diced. Three batches were prepared (two at 20 ml polymer:1 L non-solvent and one at 10 ml polymer:500 ml non-solvent) and the resulting particles were pooled. The resulted in 1.4208 g of microspheres collected, for a yield of 63.0%.

EXAMPLE 10

FLM and PIN of Plasmid DNA

FLM Procedure 200 mg of poly(fumaric-co-sebacic acid) 20:80 ("P(FA:SA) 20:80") (MW=8 kDa) was dissolved in 2 ml of methylene chloride and vortexed with 2 ml of pCMV-Bgal (1 mg/ml) in distilled water for 15 s to produce an emulsion. The emulsion was frozen in liquid nitrogen and lyophilized overnight.

Phase Inversion Nanoencapsulation

The resulting matrix was reconstituted with 4 ml of methylene chloride (5% P(FA:SA) 20:80 w/v and dispersed into petroleum ether at a 1:50 ratio of solvent to non-solvent. The resulting particulates were recovered by filtration, air-dried, and lyophilized to remove residual solvents.

Analysis

Agarose gels were run on plasmid DNA that was extracted from the microspheres and also on samples from a release study of 10 mg of microspheres in 1 ml of TE buffer, pH 7.5 at 23° C. Both samples showed a mixture of super-coiled and open-circular DNA with no evidence of degradation. The size of the PIN microspheres was generally less than 10 μm.

EXAMPLE 11

FLM and PIN of Plasmid DNA

FLM Procedure 3.0 g of P(FA:SA) 20:80 (MW=8 kDa) was dissolved in 10 ml of methylene chloride and vortexed with 1.5 ml of pCMV-Bgal in distilled water (4.5 mg/ml) for 60 s, to produce an emulsion. The emulsion was frozen in liquid nitrogen and lyophilized overnight.

Phase Inversion Nanoencapsulation

The resulting matrix was reconstituted with 100 ml of methylene chloride (5% P(FA:SA) 20:80 w/v) and dispersed into petroleum ether at a 1:50 ratio of solvent to non-solvent. The resulting particulates were recovered by filtration, air-dried, and lyophilized to remove residual solvents. Recovered were 2.5 g of spheres, an 83% yield.

The spheres were extracted in triplicate by dissolving known masses of the spheres with methylene chloride and extracting (two times) with TE buffer. The extracts were pooled and the plasmid concentration quantified by OD at 260 nm. The average loading was 196 μg±23.8 μg plasmid DNA/100 mg spheres, compared to the theoretical loading of 200 μg/100 mg spheres, for an encapsulation efficiency of 87.5%. The resulting microspheres were round and discrete with an average size of about 3 μm.

Analysis

A release study in TE buffer was performed in triplicate. The results are shown in Table 17.

TABLE 17

Cumulative Release In Vitro as a Function of Time

| Time (hrs) | % Cumulative Release | S.E. |
|---|---|---|
| 0.75 | 47.8 | 6.3 |
| 1.75 | 53.5 | 4.2 |
| 2.75 | 54.1 | 3.4 |
| 9 | 57.0 | 0.7 |
| 19 | 59.8 | 3.2 |
| 26 | 66.8 | 1.8 |
| 46 | 73.8 | 0.3 |
| 96 | 76.7 | 1.7 |

Agarose gels were run on plasmid DNA that was extracted from the microspheres and also on samples from a release study of 10 mg of microspheres in 1 ml of TE buffer, pH 7.5 at 23° C. Both samples showed a mixture of super-coiled and open-circular DNA with no evidence of degradation.

EXAMPLE 12

FLM and PIN of Plasmid DNA

FLM Procedure 1.5 g of P(FA:SA) 20:80 (MW=8 kDa) was dissolved in 10 ml of methylene chloride and vortexed with 1.0 ml of VR-1223 Vical plasmid with reporter gene for luciferase in 0.9% sodium chloride (3.6 mg/ml) for 60 s to produce an emulsion. The emulsion was frozen in liquid nitrogen and lyophilized overnight.

Phase Inversion Nanoencapsulation

The resulting matrix was reconstituted with 50 ml of methylene chloride (3% P(FA:SA) 20:80 (w/v) (MW=8 kDa)) and dispersed into petroleum ether at a 1:80 ratio of solvent to non-solvent. The particulates were recovered by filtration, air-dried, and lyophilized to remove residual solvents. Recovered were 1.1 g of spheres, a 73% yield. The resulting microspheres were round and discrete with an average size of about 3 μm.

Analysis

A release study in TE buffer was performed in triplicate. The results are shown in Table 18.

TABLE 18

Cumulative Release In Vitro as a Function of Time

| Time (hrs) | % Cumulative Release | S.E. |
|---|---|---|
| 1 | 10.9 | 8.6 |
| 3 | 14.5 | 10.2 |
| 5 | 17.3 | 10.4 |
| 11 | 24.6 | 7.4 |
| 23 | 38.6 | 10.0 |
| 29 | 57.3 | 7.4 |
| 119 | 67.0 | 1.2 |

Agarose gels were run on plasmid DNA that was extracted from the microspheres and also on samples from a release study of 10 mg of microspheres in 1 ml of TE buffer, pH 7.5 at 23° C. Both samples showed a mixture of super-coiled and open-circular DNA with no evidence of degradation.

EXAMPLE 13

FLM and PIN of Plasmid DNA

FLM Procedure 1.0 g of P(FA:SA) 20:80 (MW=8 kDa) was dissolved in 10 ml of methylene chloride and vortexed with 1.0 ml of 10B plasmid with LDL receptor gene in TE buffer (2.3 mg/ml) for 60 s, to produce an emulsion. The emulsion was frozen in liquid nitrogen and lyophilized overnight.

Phase Inversion Nanoencapsulation

The resulting matrix was reconstituted with 33 ml of methylene chloride (3% P(FA:SA) 20:80 (w/v) (MW=8 kDa)) and dispersed into petroleum ether at a 1:80 ratio of solvent to non-solvent. The particulates were recovered by filtration, air-dried, and lyophilized to remove residual solvents. Recovered were 0.9 g of spheres, a 90% yield. The resulting microspheres were round and discrete with an average size of about 3 µm.

Analysis

A release study in TE buffer was performed in duplicate. The results are shown in Table 19.

TABLE 19

Cumulative Release In Vitro as a Function of Time

| Time (hrs) | % Cumulative Release | S.E. |
|---|---|---|
| 1 | 26.0 | 5.7 |
| 3 | 31.2 | 3.6 |
| 5 | 37.9 | 2.9 |
| 11 | 42.2 | 5.4 |
| 23 | 48.1 | 7.9 |
| 29 | 56.5 | 3.9 |
| 119 | 78.4 | 13.6 |

Agarose gels were run on plasmid DNA that was extracted from the microspheres and also on samples from a release study of 10 mg of microspheres in 1 ml of TE buffer, pH 7.5 at 23° C. Both samples showed a mixture of super-coiled and open-circular DNA with no evidence of degradation.

EXAMPLE 14

Growth Hormone Zinc Precipitation

Complexation of growth hormone ("GH") to zinc was performed using a procedure modified from that described in U.S. Pat. No. 5,667,808 to Johnson et al. First, 500 µl stock GH and 4500 µl 4 mM sodium bicarbonate were dripped into 5000 µl 0.9 mM zinc acetate to form a GH-zinc precipitate. This precipitate was then centrifuged, the supernatant removed, and TWEEN™ 20 at 0.05% (v/v) was added. A PIN process then was utilized to microencapsulate the particles of GH-zinc. This procedure, which is described herein, was performed with batch sizes of 1 mg, 10, mg, 20 mg, and 40 mg GH.

Complexation efficiency (BCA protein quantification) data is shown below in Table 20.

TABLE 20

| BCA Protein Quantification | |
|---|---|
| Blank H$_2$O | 0 |
| 0.9 mM zinc acetate | 0.002 |
| 4 mM sodium bicarbonate | 0.003 |

TABLE 20-continued

| BCA Protein Quantification | |
|---|---|
| supernatant following centrifugation | 0.008 |
| resuspended GH-Zn pellet | 1.313 |

The results indicate approximately 100% complexation.

EXAMPLE 15

Stability of FcOPG in Freeze-Emulsion Polymer Matrices and Testing of FcOPG Extraction Procedures Osteoprotegerin (OPG) is a naturally occurring cytokine, a protein with protective function towards bone. Amgen's recombinant version of OPG is coupled to FC to facilitate separation during production and is a dimer linked by disulfide bonds. The monomer has an average mass of 45.3 kDa from addition of amino acids derived from the sequence. The protein was used as supplied from Amgen without any additional excipients or stabilizers with generally good results. In all cases, the protein was incorporated into the polymer in the liquid state, using either simple emulsions at different oil:water ratios or the "frozen-emulsion" technique described herein.

Freeze-emulsion matrices were prepared with three different polymers and then extracted to test the stability of FcOPG when dispersed as solid particles in polymer. Each formulation used 60 mg of polymer in 1 ml of methylene chloride (6% w/v), to which 0.116 ml of stock FcOPG (9.18 mg/ml) containing 1.06 mg of FcOPG added. The protein solution was emulsified in the polymer solution by vortexing for 30 s at maximum amplitude or else with a combination of vortexing for 30 s and probe sonication for 5 s at 25% amplitude with the microtip. The loading of FcOPG was 1.74% (w/w) and the w/o ratio was approximately 1:10. The emulsion was immediately frozen for 5 min. in liquid nitrogen and lyophilized for 24 hrs.

The effect of the micronization treatments on FcOPG when polymer was not included and the vortexing and vortexing/probe-sonication treatments were performed in methylene chloride only was also tested. For these experiments, the FcOPG following the freeze-emulsion procedure was resuspended in 0.5 ml of 10 mM glutamate, pH 5.0, 3.5% mannitol (w/v), 0.01% TWEEN™ 20 (v/v) and 0.03% sodium azide (Amgen Formulation Buffer ("AFB")). No extraction procedure was required since polymer matrix was not present.

Also tested in this set of experiments was the efficiency of extraction of FcOPG using three different methods: oil/water extraction (O/W); oil/oil extraction (O/O) and "rapid release" (RR). O/W extraction was performed by dissolving approximately 8–10 mg of freeze-emulsion matrix in 0.7 ml of methylene chloride and extracting with 0.5 ml of AFB. O/O extraction was performed by dissolving approximately 8–10 mg of freeze-emulsion matrix in 1.4 ml of a 1:1 mixture of methylene chloride:methyl ethyl ketone (MEK) pelleting the insoluble protein by centrifugation at 15K rpm for 10 min, discarding the supernatant organic fluids and resuspending the air-dried pellet in 0.5 ml of AFB. RR was done by a combination of vortexing and agitating approximately 8–10 mg of freeze-emulsion matrix in 0.5 ml of AFB for 2 hrs at room temperature. The design of the experiment is indicated in Table 21.

TABLE 21

| Polymer | Experimental Variables | |
|---|---|---|
| | Micronization Treatment | Extraction Protocol |
| None (MeCl$_2$) | Vortex | O/W |
| | | O/O |
| | | R/R |
| | Vortex and Probe Sonication | O/W |
| | | O/O |
| | | R/R |
| P(FA:SA) 20:80 | Vortex | O/W |
| | | O/O |
| | | R/R |
| | Vortex and Probe Sonication | O/W |
| | | O/O |
| | | R/R |
| PLGA 50:50 RG502H | Vortex | O/W |
| | | O/O |
| | | R/R |
| | Vortex and Probe Sonication | O/W |
| | | O/O |
| | | R/R |
| PLA 24 kDA | Vortex | O/W |
| | | O/O |
| | | R/R |
| | Vortex and Probe Sonication | O/W |
| | | O/O |
| | | R/R |

The results of this experiment are shown in Table 22.

TABLE 22

Effect of Polymer and Process on FcOPG Molecular Weight

| | | Apparent FcOPG Molecular Weight (kDA) | | | | | |
|---|---|---|---|---|---|---|---|
| | | Reducing Gel | | | Non-Reducing Gel | | |
| Polymer | Micronize | O/W | O/O | R/R | O/W | O/O | R/R |
| None | V | | 45 | | | 90 | |
| | V + S | | 45 | | | 90 | |
| ??* | V | 45 | 45 | ND | 90 | 90 | ND |
| | V + S | ND | Agg | ND | ND | 90* | ND |
| PLGA 50:50 RG502H | V | 45 | 45 | 45 | 90 | 90 | 90 |
| | V + S | ND | 45 | 45 | ND | 90 | 90 |
| PLA 24 kDA | V | 45 | 45 | 45 | 90 | 90 | 90 |
| | V + S | ND | 45 | 45 | 90 | 90 | 90 |

Agg = aggregate;
*= slight amount detected;
V = vortex for 30 sec;
V + S = vortex for 30 sec followed by probe sonication for 5 sec at amplitude 25 with the microtip.
ND = not detected The vortex and vortex-sonication treatments had no effect on FcOPG when no polymer and only methylene chloride was used during the freeze-emulsion process. Under reducing conditions the protein migrated like stock FcOPG at approximately 45 kDA and non-reducing conditions, the protein migrated like stock FcOPG at an apparent molecular weight of approximately 90 kDA. In no instance was aggregation observed, and the amount of protein resolubilized in AFB appeared to be the same.

Vortex treatment had negligible effect on FcOPG during the freeze-emulsion procedure, regardless of the polymer used. However, substantially less FcOPG was recovered following vortex-sonication treatments, independent of the polymer or extraction protocol used. In particular, the recovery of FcOPG from P(FA:SA) 20:80 following vortex-sonication treatment was always poor, indicating an irreversible association of the protein with the polymer or else aggregation, as indicated in the table. Consequently, it was decided that most of the formulations would be prepared with PLGA, an accepted biomedical polymer and that bioadhesive properties would be introduced into the final formulation by blending with bioadhesive excipients.

Of the three extraction procedures tested, the O/O method appeared to result in the highest recovery of FcOPG, followed by the O/W method and lastly R/R. The O/O procedure was used as the default extraction procedure for most of the formulations.

EXAMPLE 16

Encapsulation of FcOPG in P(FA:SA)

The purpose of this experiment was to test the effect of the frozen emulsion micronization step followed by PIN on integrity of FcOPG and to determine the effect of polymer matrix on release kinetics. A loading of 3.4% FcOPG w/w in P(FA:SA) 20:80 (MW approximately 7 kDA) was used.

Micronization Methods.

First, 0.3 g of P(FA:SA) 20:80 solid was dissolved in 5 ml of methylene chloride yielding a 6% solution (w/v). Then, 1.15 ml of stock FcOPG, containing 10.56 mg FcOPG (9.18 mg/ml), was thawed from storage at −80° C. and added to 5 ml of the polymer solution. The water:oil emulsion ratio was approximately 1:5. The mixture was vortexed for 30 s at maximum amplitude, and immediately frozen in liquid nitrogen for 5 min. The frozen mixture was lyophilized for 24 hrs.

Encapsulation Methods.

The dried emulsion matrix was redissolved in a fresh 5 ml volume of methylene chloride, vortexed for 2 min, and then dispersed into 250 ml of petroleum ether. Particles were collected by vacuum filtration with a P8 quantitative filter, air-dried, and weighed. Approximately 0.2872 g of the starting material was recovered, equivalent to 92.5% recovery.

EXAMPLE 17

Encapsulation of FcOPG in PLGA 50:50

The experiment was performed essentially identically to Example 16, except that PLGA 50:50 RG502H (MW approximately 12 kDa) was the polymer used. Approximately 0.2937 g of the starting material was recovered, equivalent to 94.6% recovery.

EXAMPLE 18

Encapsulation of FcOPG in PLA

The experiment was performed essentially identically to Example 16, except that PLA (MW approximately 24 kDa) was the polymer used. Approximately 0.2307 g of the starting material was recovered, equivalent to 74.3% recovery.

EXAMPLE 19

FLM of FcOPG in PLGA 50:50, 3.4% Loading

This experiment is the first of a series of three formulations to test the effect of different water:oil (o:w) ratios and loadings on emulsion-freeze micronization followed by encapsulation of FcOPG using the PIN process. Polymer and loading were as in Example 17.

Micronization Methods.

First, 0.3 g of PLGA solid was dissolved in 5 ml of methylene chloride yielding a 6% solution (w/v). Then, 1.15 ml of stock FcOPG, containing 10.56 mg FcOPG (9.18 mg/ml), was taken from storage at −80° C. and lyophilized for 24 hrs. The residue from each vial was redissolved in 0.3 ml of 0.1M PBS, pH7.2, vortexed for 30 s, and added to 5 ml of polymer solution. The water:oil emulsion ratio was approximately 3:50. The mixture was vortexed for 60 s at maximum amplitude, and immediately frozen in liquid nitrogen for 5 min. The frozen mixture was lyophilized for 24 hrs.

Encapsulation Methods.

The dried emulsion matrix was redissolved in a fresh 5 ml volume of methylene chloride, vortexed for 2 min., and then dispersed into 250 ml of petroleum ether. Particles were collected by vacuum filtration with a P8 quantitative filter, frozen, lyophilized, and weighed. Approximately 0.3084 g of the starting material was recovered, equivalent to 99.3% recovery.

EXAMPLE 20

FLM of FcOPG in PLGA 50:50, 6.58% Loading

The experiment was performed essentially identically to Example 19, except that the loading of FcOPG was 6.58%, achieved by using two vials of the stock FcOPG. Approximately 0.32112 g of the starting material was recovered, equivalent to 85.7% recovery.

EXAMPLE 21

FLM of FcOPG in PLGA 50:50, 9.55% Loading

The experiment was performed essentially identically to Example 19, except that the loading of FcOPG was 6.58%, achieved by using three vials of the stock FcOPG. Also, in this experiment, the residue from each vial was redissolved in a total of 0.45 ml of 0.1M PBS, pH 7.2, yielding a water:oil emulsion ratio of approximately 9:100. Approximately 0.33168 g of the starting material was recovered, equivalent to 103.11 % recovery.

EXAMPLE 22

FLM of FcOPG in PLGA 50:50, W:O Ratio 11:50

This experiment is the first of a series of four formulations to test the effect of different water:oil (o:w) ratios and loadings on emulsion-freeze micronization followed by encapsulation of FcOPG using the PIN process. A loading of 3.4% FcOPG w/w in PLGA 50:50 RG 502H (MW approximately 12 kDA) was used.

Micronization Methods.

First, 0.3 g of PLGA solid was dissolved in 5 ml of methylene chloride yielding a 6% solution (w/v). One vial with 1.15 ml of stock FcOPG, containing 10.56 mg FcOPG (9.18 mg/ml), was thawed from storage at −80° C. and added to 5 ml of polymer solution. The water:oil emulsion ratio was approximately 11:50. The mixture was vortexed for 30 s at maximum amplitude, and immediately frozen in liquid nitrogen for 5 min. The frozen mixture was lyophilized for 24 hrs.

Encapsulation Methods.

The dried emulsion matrix was redissolved in a fresh 5 ml volume of methylene chloride, vortexed for 2 min then dispersed into 250 ml of petroleum ether. Particles were collected by vacuum filtration with a P8 quantitative filter, frozen, lyophilized and weighed. Approximately 0.31056 g of the starting material was recovered, equivalent to 56.3% recovery.

EXAMPLE 23

FLM of FcOPG in PLGA 50:50, W:O Ratio 22:50

The experiment was performed essentially identically to Example 22, except that the loading of FcOPG was 6.6%, achieved by using two vials of the stock FcOPG. The water:oil emulsion ratio was approximately 22:50. Approximately 0.32112 g of the starting material was recovered, equivalent to 97.1 % recovery.

EXAMPLE 24

FLM of FcOPG in PLGA 50:50, W:O Ratio 33:50

The experiment was performed essentially identically to Example 22, except that the loading of FcOPG was 9.6%, achieved by using three vials of the stock FcOPG. The water:oil emulsion ratio was approximately 33:50. Approximately 0.33168 g of the starting material was recovered, equivalent to 119.5% recovery.

EXAMPLE 25

FLM of FcOPG in PLGA 50:50, W:O Ratio 44:50

The experiment was performed essentially identically to Example 22, except that the loading of FcOPG was 12.3%, achieved by using four vials of the stock FcOPG. The water:oil emulsion ratio was approximately 44:50. Approximately 0.5154 g of the starting material was recovered, equivalent to 150.6% recovery. The sample probably was incompletely lyophilized.

EXAMPLE 26

FLM of FcOPG in PLGA 50:50 Without Lethicin

This experiment is the first of a series of two formulations to test the effect of lecithin on stabilizing the protein emulsion during the emulsion-freeze micronization step, and encapsulation of FcOPG using the PIN process with a different solvent-non-solvent pair. A loading of 3.4% FcOPG w/w in PLGA 50:50 RG 502H (MW approximately 12 kDA) was used.

Micronization was carried out as in Example 22. For encapsulation, the dried emulsion matrix then was redissolved in a fresh 5 ml volume of ethyl acetate, vortexed for 2 min, and then dispersed into 45 ml of isopropanol. A 7 ml portion of the formulation was frozen in liquid nitrogen for 15 min., lyophilized for 3 days.

EXAMPLE 27

Frozen Emulsion Encapsulation of FcOPG in PLGA 50:50 With Lethicin

The experiment was performed essentially identically to Example 26, except that the methylene chloride contained 10 mg lecithin (2 mg lecithin/ml). A loading of FcOPG was 3.29% was achieved.

EXAMPLE 28

FLM of FcOPG in PLGA 50:50

The experiment is the first of a series of three formulations to test the effect of lecithin on stabilizing the protein emulsion during the emulsion-freeze micronization step. The use of probe sonication to reduce emulsion size during the micronization step was also tested, as well as encapsulation of FcOPG using the PIN process with methylene chloride and petroleum ether as the solvent-non-solvent pair. A loading of 2.9% FcOPG w/w in PLGA 50:50 RG 502H (MW approximately 12 kDA) was used.

Micronization Methods.

First, 0.3 g of PLGA solid was dissolved in 5 ml of methylene chloride yielding a 6% solution (w/v). One vial with 0.92 ml of stock FcOPG, at a concentration of 26.9 mg/ml, was thawed from storage at −80° C. Then, 0.3 ml of the stock solution containing 8.97 mg of FcOPG was added to 5 ml of polymer solution, to which no lecithin was added. The water:oil emulsion ratio was approximately 3:50. The mixture was vortexed for 30 s at maximum amplitude, probe-sonicated for 5 s at 25% amplitude and immediately frozen in liquid nitrogen for 5 min. The frozen mixture was lyophilized for 24 hrs.

Encapsulation Methods.

The dried emulsion matrix was redissolved in a fresh 5 ml volume of methylene chloride, vortexed for 2 min., and then dispersed into 250 ml of petroleum ether. Particles were collected by vacuum filtration with a P8 quantitative filter, frozen, lyophilized, and weighed. Approximately 0.2876 g of the starting material was recovered, equivalent to 93.1 % recovery.

EXAMPLE 29

FLM of FcOPG in PLGA 50:50

The experiment was performed essentially identically to Example 28, except that the loading of FcOPG was 2.68% and 25 mg lecithin (5 mg lecithin/ml) was included in the polymer solution to give a lecithin loading of 7.49% w/w. For the encapsulation, the dried emulsion matrix was redissolved in a fresh 5 ml volume of methylene chloride, vortexed for 2 min., and then dispersed into 250 ml of petroleum ether. Particles were coalesced on the filter after attempts were made to vacuum filter with a P8 quantitative filter.

EXAMPLE 30

FLM of FcOPG in PLGA 50:50

The experiment was performed essentially identically to Example 29, except that the loading of FcOPG was 2.49% and 50 mg lecithin (10 mg lecithin/ml) was included in the polymer solution to give a lecithin loading of 13.92% w/w.

A summary of the process variables and the theoretical vs. actual FcOPG loading for the formulations made in Examples 16–30 is provided in Tables 23 and 24, respectively. Table 25 summarizes the results of Coulter size distributions, and Table 26 summarizes the SEM morphological studies, of these formulations. Table 27 and 28 respectively summarize the SEC HPLC/SDS-PAGE and the FcOPG release for these formulations.

TABLE 23

Summary of Process Variables for Examples 16–30

| Example | Polymer | % FcOPG (w/w) | Incorporation into Polymer |
|---|---|---|---|
| 16 | P(FA:SA) 20:80 | 3.4% | Vortex, fr./em. (~1:5, w:o) |
| 17 | PLGA RG 502H | 3.4% | Vortex, fr./em. (~1:5, w:o) |
| 18 | PLA 24 kDA | 3.4% | Vortex, fr./em. (~1:5, w:o) |
| 19 | PLGA RG 502H | 3.4% | Vortex, fr./em. (~3:50, w:o) |
| 20 | PLGA RG 502H | 6.6% | Vortex, fr./em. (~3:50, w:o) |
| 21 | PLGA RG 502H | 9.6% | Vortex, fr./em. (~9:100, w:o) |
| 22 | PLGA RG 502H | 3.4% | Vortex, fr./em. (~11:50, w:o) |
| 23 | PLGA RG 502H | 6.6% | Vortex, fr./em. (~22:50, w:o) |
| 24 | PLGA RG 502H | 9.6% | Vortex, fr./em. (~33:50, w:o) |
| 25 | PLGA RG 502H | 12.3% | Vortex, fr./em. (~44:50, w:o) |
| 26 | PLGA RG 502H | 3.4% | Vortex, fr./em. (~3:50, w:o) |
| 27 | PLGA RG 502H | 3.3% | Vortex, fr./em. (~3:50, w:o) |
| 28 | PLGA RG 502H | 2.9% | Vortex/sonicate, fr./em. (~3:50, w:o) |
| 29 | PLGA RG 502H | 2.7% | Vortex, fr./em. (~3:50, w:o) |
| 30 | PLGA RG 502H | 2.5% | Vortex, fr./em. (~3:50, w:o) | fr./em. = frozen emulsion

TABLE 24

Theoretical & Actual Loading of FcOPG for Examples 16–30

| Example | Polymer | theor. loading (µg/mg spheres) | recovered (µg/mg spheres) | % Recovery |
|---|---|---|---|---|
| 16 | P(FA:SA) 20:80 | 34 | 30.2 ± 9.2 | 88.8% |
| 17 | PLGA RG 502H | 34 | 35.8 ± 12.3 | 105.3% |
| 18 | PLA 24 kDA | 34 | 28.4 ± 4.2 | 83.5% |
| 19 | PLGA RG 502H | 34 | 17.5 ± 1.0 | 51.5% |
| 20 | PLGA RG 502H | 66 | 15.6 ± 2.5 | 23.6% |
| 21 | PLGA RG 502H | 96 | 25.5 ± 1.0 | 26.6% |
| 22 | PLGA RG 502H | 34 | 23.0 | 67.7 |
| 23 | PLGA RG 502H | 66 | 46.8 | 70.9 |
| 24 | PLGA RG 502H | 96 | 112.4 | 117.1 |
| 25 | PLGA RG 502H | 123 | 62.8 | 51.1 |
| 26 | PLGA RG 502H | 34 | — | — |
| 27 | PLGA RG 502H | 33 | — | — |

TABLE 24-continued

Theoretical & Actual Loading of FcOPG for Examples 16–30

| Example | Polymer | theor. loading (μg/mg spheres) | recovered (μg/mg spheres) | % Recovery |
|---|---|---|---|---|
| 28 | PLGA RG 502H | 29 | 10.2 | 35.3 |
| 29 | PLGA RG 502H | 27 | — | — |
| 30 | PLGA RG 502H | 25 | 16.5 | 66.1 |

TABLE 25

Coulter Size Distribution of Formulations of Examples 16–30

| | | Number | | Surface Area | | Volume | |
|---|---|---|---|---|---|---|---|
| Ex. | Polymer | mean | median | mean | median | mean | median |
| 16 | P(FA:SA) 20:80 | 0.0788 | 0.105 | 2.181 | 1.113 | 9.134 | 4.631 |
| 17 | PLGA RG 502H | 0.295 | 0.184 | 2.935 | 1.729 | 8.405 | 5.218 |
| 18 | PLA 24 kDA | 0.284 | 0.238 | 1.158 | 0.448 | 11.72 | 4.169 |
| 19 | PLGA RG 502H | 0.154 | 0.0998 | 8.452 | 2.004 | 104.4 | 34.27 |
| 20 | PLGA RG 502H | 0.121 | 0.0846 | 9.733 | 1.843 | 79.25 | 44.0 |
| 21 | PLGA RG 502H | 0.124 | 0.0851 | 7.192 | 2.568 | 24.82 | 21.56 |
| 22 | PLGA RG 502H | 0.150 | 0.0936 | 6.334 | 2.842 | 19.42 | 15.11 |
| 23 | PLGA RG 502H | 0.134 | 0.0870 | 7.997 | 2.420 | 74.22 | 21.34 |
| 24 | PLGA RG 502H | 0.131 | 0.0880 | 9.326 | 2.240 | 92.12 | 34.15 |
| 25 | PLGA RG 502H | 0.492 | 0.381 | 5.337 | 2.610 | 14.08 | 12.06 |
| 26 | PLGA RG 502H | 0.158 | 0.0818 | 0.490 | 0.389 | 1.374 | 0.542 |
| 27 | PLGA RG 502H | 0.0680 | 0.109 | 0.359 | 0.367 | 0.444 | 0.444 |
| 28 | PLGA RG 502H | 0.102 | 0.0803 | 6.668 | 0.542 | 50.29 | 57.38 |
| 29 | PLGA RG 502H | — | — | — | — | — | — |
| 30 | PLGA RG 502H | 0.575 | 0.389 | 4.083 | 2.716 | 10.10 | 8.218 |

TABLE 26

SEM Morphologies of the Formulations of Examples 16–30

| | | Size (μm) | | | Morphology | | |
|---|---|---|---|---|---|---|---|
| Ex. | Polymer | min. | max. | mean | min. | max. | mean |
| 16 | P(FA:SA) 20:80 | 0.6 | 5 | 1 | Yes | Yes | Yes |
| 17 | PLGA RG 502H | <0.1 | 2 | 0.2 | Yes | Yes | No |
| 18 | PLA 24 kDA | <0.1 | 1 | 0.2 | Yes | Yes | No |
| 19 | PLGA RG 502H | 0.1 | 5 | 0.3 | Yes | Yes | No |
| 20 | PLGA RG 502H | 0.1 | 5 | 0.3 | Yes | Yes | No |
| 21 | PLGA RG 502H | 0.1 | 5 | 0.3 | Yes | Yes | No |
| 22 | PLGA RG 502H | 0.1 | 5 | 0.3 | Most | Most | No |
| 23 | PLGA RG 502H | 0.1 | 5 | 0.3 | Yes | Yes | No |
| 24 | PLGA RG 502H | 0.1 | 5 | 0.3 | Most | Most | No |
| 25 | PLGA RG 502H | 0.1 | 10 | 0.3 | Some | Some | No |
| 26 | PLGA RG 502H | 0.1 | 0.3 | 0.2 | Yes | Yes | No |
| 27 | PLGA RG 502H | 0.1 | 0.3 | 0.2 | Yes | Yes | No |
| 28 | PLGA RG 502H | — | — | — | — | — | — |
| 29 | PLGA RG 502H | — | — | — | — | — | — |
| 30 | PLGA RG 502H | 0.1 | 2 | 0.4 | Yes | Yes | No |

TABLE 27

SEC HPLC/SDS-PAGE for the Formulations of Examples 16–30

| | | SEC-HPLC (Mw (kDa)) | | SDS PAGE (Apparent MW (kDa)) | |
|---|---|---|---|---|---|
| Ex. | Polymer | major peak | minor peak | reducing | non-reducing |
| 16 | P(FA:SA) 20:80 | 12.5 | 9 | ~45, ~90 small | ~90 |
| 17 | PLGA RG 502H | 78 | — | ~45, ~90 small | ~90 |
| 18 | PLA 24 kDA | 78 | — | ~45, ~90 small | ~90 |
| 19 | PLGA RG 502H | 78 | — | ~45 | Not done |
| 20 | PLGA RG 502H | 78 | — | ~45 | Not done |
| 21 | PLGA RG 502H | 78 | — | ~45 | Not done |
| 22 | PLGA RG 502H | 78 | — | ~45 | ~45, ~90 |
| 23 | PLGA RG 502H | 78 | — | ~45 | ~45, ~90 |
| 24 | PLGA RG 502H | 78 | — | ~45 | ~45, ~90 |
| 25 | PLGA RG 502H | 78 | — | ~45 | ~45, ~90 |
| 26 | PLGA RG 502H | — | ~50 | ND | Not Detected |
| 27 | PLGA RG 502H | C | Not done | Not done | Not done |
| 28 | PLGA RG 502H | 78 | ~50 | ~45 | ~45, ~90 |
| 29 | PLGA RG 502H | — | — | — | — |
| 30 | PLGA RG 502H | 78 | ~50 | — | — |
| | FcOPG Stock | 78 | — | ~45 | ~90 |

TABLE 28

FcOPG Release From the Formulations of Examples 16–30

Percent Total FcOPG Released ± SEM

| Ex | Polymer | 1 hr | 3 hr | 5/6 hr* | 22 hr | 74/94 hr* |
|---|---|---|---|---|---|---|
| 16 | P(FA:SA) 20:80 | 35.0 ± 12.2 | 45.5 ± 9.1 | 64.1 ± 5.1* | 73.0 ± 1.7 | 87.9 ± 4.7* |
| 17 | PLGA RG 502H | 45.2 ± 17.3 | 58.2 ± 19.8 | 61.2 ± 18.0* | 69.9 ± 12.7 | 95.0 ± 1.1* |
| 18 | PLA 24 kDA | 52.5 ± 3.2 | 63.6 ± 3.0 | 72.5 ± 2.4* | 80.8 ± 1.9 | 92.3 ± 2.1* |
| 19 | PLGA RG 502H | 68.5 ± 5.7 | 84.3 ± 5.2 | 89.5 ± 5.1 | 92.8 ± 4.7 | 94.5 ± 4.7 |
| 20 | PLGA RG 502H | 65.4 ± 4.8 | 79.4 ± 2.6 | 89.2 ± 0.4 | 94.1 ± 1.2 | 96.0 ± 1.0 |
| 21 | PLGA RG 502H | 74.0 ± 0.1 | 85.1 ± 1.6 | 88.7 ± 1.4 | 94.1 ± 1.2 | 96.0 ± 1.0 |
| 22 | PLGA RG 502H | 91.9 ± 2.7 | 97.2 ± 0.6 | 97.9 ± 0.6 | 98.0 ± 0.7 | — |
| 23 | PLGA RG 502H | 82.9 ± 4.0 | 94.6 ± 2.4 | 96.8 ± 0.8 | 96.7 ± 0.8 | — |
| 24 | PLGA RG 502H | 90.2 ± 1.7 | 98.2 ± 0.2 | 98.9 ± 0.1 | 99.0 ± 0.1 | — |
| 25 | PLGA RG 502H | 83.2 ± 1.3 | 96.4 ± 0.5 | 98.3 ± 0.2 | 98.7 ± 0.2 | — |
| 26 | PLGA RG 502H | — | — | — | — | — |
| 27 | PLGA RG 502H | — | — | — | — | — |
| 28 | PLGA RG 502H | 62.2 ± 1.3 | 79.5 ± 3.0 | 91.8 ± 3.0 | 93.8 ± 1.2 | — |
| 29 | PLGA RG 502H | — | — | — | — | — |
| 30 | PLGA RG 502H | 76.7 ± 5.1 | 86.7 ± 4.1 | 90.8 ± 4.6 | 96.5 ± 1.7 | — |

*bolded values are at the indicated bolded time points

EXAMPLE 31

FcOPG Release Study Performed with SEC-HPLC

Approximately 6–20 mg aliquots of microspheres from Examples 22, 23, 24, 25, 28, and 30 were incubated at 37° C. in 1 ml of 0.1 M PBS, pH 7.2 with 0.003% sodium azide. At intervals of 1, 3, 5, and 24 hrs, the spheres were centrifuged at 15 KG-average for 5 min., the supernatant release fluids collected, and the residual spheres resuspended in 1 ml of fresh PBS. After the final time point, the microspheres were extracted with the O/O procedure and the protein pellet resuspended in 1 ml of fresh PBS.

Then, 0.2 ml of the release fluids was mixed with 10 μL of ethylene glycol (internal standard) and HPLC was performed. FcOPG standards prepared by dilution of the stock 9.18 mg/ml solution (supplied by Amgen) also were run at concentrations of 62.5, 125, 250, 500, and 1000 μg/ml. The area under standard FcOPG peaks (Rf approximately 7.9 min) was integrated and a calibration curve was constructed relating the concentration of FcOPG to area. The concentration of samples was calculated from the relationship and used to measure the release of these formulations.

With the exception of Examples 22 and 30, all the formulations tested had FcOPG that migrated like stock FcOPG with an apparent molecular weight of 77,000. Example 22 had some native FcOPG along with a substantial amount of aggregated FcOPG which migrated with a retention time of approximately 6.9 min., equivalent to an apparent MW of 145,000. Example 30 had mostly native FcOPG along with a substantial amount of aggregate with retention time of approximately 4.9 min., corresponding to an apparent molecular weight of 858,000. For both examples 22 and 30, the amount of aggregated protein, presumably FcOPG, was not used for calculations of release. The results are shown in Table 29 and in FIGS. 1–4.

TABLE 29

Cumulative FcOPG Released (μg FcOPG/mg microspheres)

| Time (hrs) | Ex. 8 | Ex. 9 | Ex. 10 | Ex. 11 | Ex. 14 | Ex. 16 |
|---|---|---|---|---|---|---|
| 0 | 0 | 0 | 0 | 0 | 0 | 0 |
| 1 | 23.0 | 40.6 | 98.3 | 51.0 | 7.6 | 15.2 |
| 3 | 23.0 | 46.6 | 111.7 | 61.5 | 10.0 | 16.3 |
| 5 | 23.0 | 46.8 | 112.4 | 62.8 | 10.2 | 16.5 |
| 24 | 23.0 | 46.8 | 112.4 | 62.8 | 10.2 | 16.5 |
| Extracted | 0 | 0 | 0 | 0 | 0 | 0 |
| Total | 23.0 | 46.8 | 112.4 | 62.8 | 10.2 | 16.5 |
| Theoretical | 34 | 66 | 96 | 123 | 29 | 25 |
| % Theoretical | 67.7 | 70.9 | 117.1 | 51.1 | 35.3 | 66.1 |

EXAMPLE 32

Human Growth Hormone Particle Size

To determine the drug particle size following the FLM process, the encapsulating polymer material was redissolved in methylene chloride and the insoluble particulates (human growth hormone and stabilizing excipients) were sized using Coulter LS 230 laser diffraction. The ingredient composition used to produce the FLM was 67.7%PLGA (50:50 Mw 12K), 2.1% human growth hormone, 13.3% FeO, 2.3% mannitol, 0.2% Pluronic™ F127 and 14.4% sucrose. An aqueous phase (2.5 ml) containing the human growth hormone, sucrose, mannitol, and Pluronic™ F127 was vortexed with the ethyl acetate phase (10 ml) containing PLGA for 1 minute and flash frozen in liquid nitrogen for 15 minutes. The frozen mixture was lyophilized with a Titan Cold Trap (FTS Kinetics, Stone Ridge, N.Y.) for 48 hours. The lyophilized matrix was subsequently fabricated into microspheres using the PIN process.

The volume mean of the drug particles following FLM was 3.156±1.6 μm. The number mean of the drug particles was 1.022±2.00 μm. The differential size distributions are as follows:

TABLE 30

Size Distribution of Growth Hormone Particles.

Volume Distribution

| 10% | 25% | 50% | 75% | 90% |
|---|---|---|---|---|
| 1.726 | 2.354 | 3.273 | 4.438 | 5.616 |

Number Distribution

| 10% | 25% | 50% | 75% | 90% |
|---|---|---|---|---|
| 0.436 | 0.529 | 1.007 | 1.800 | 2.623 |

The results indicate that the human growth hormone was successfully micronized where 90% of the particulates were less than 2.623 μm in size.

EXAMPLE 33

Process Variables Affecting hGH Aggregation

Protocol

Stock solutions of hGH (20 mg/ml) were incorporated into PLGA 50:50 (Mw approximately 11 kDa) using FLM under a number of different conditions (solvent selection, vortex duration, surfactant selection & surfactant concentration) to evaluate the effects on hGH aggregation during the FLM process. Specifically, a stock solution of hGH (20mg/ml) with variable quantities of PLURONIC™ F127 or polyethylene(20) sorbitan monolaurate (TWEEN™ 20) was added to the aqueous hGH phase and vortexed for either 15 or 60 s in PLGA dissolved in either methylene chloride or ethyl acetate (50 mg/ml) and quenched in liquid nitrogen. This frozen emulsion was then lyophilized for 48 hrs to remove both the aqueous and organic solvent. Subsequently, the resulting matrix was suspended in a buffer and the supernatant analyzed at 1 and 24 hrs following hydration for hGH aggregation using SEC-HPLC.

Results.

Monomer hGH migrates at approximately 14 min. and aggregate forms are seen between 8 and 13 min. Under the same fabrication conditions, the use of ethyl acetate as the solvent provides significantly lower aggregation of GH compared to methylene chloride. Moreover, the percent aggregation did not change between 1 and 24 hrs following exposure to ethyl acetate, whereas the percent aggregation increased with time using methylene chloride. The best formulation combination appears to be through the use of ethyl acetate as the solvent, with stock GH containing 0.2% F127 with an agitation time of 15 s, which resulted in 0.7% aggregation (see Table 31).

TABLE 31

Percent hGH Aggregation Using Different Solvents

Percent Aggregation (SEC-HPLC) @ [1 hr/24 hr]-methylene chloride

| Agitation | 0.05% F127 | 0.2% F127 | 0.05% F127 + T20 | 0.2% F127 + T20 |
|---|---|---|---|---|
| 15 s vortex | 2.0/4.5 | 2.4/5.0 | 2.2/2.7 | 3.7/8.8 |
| 60 s vortex | 2.1/4.8 | 4.2/7.0 | 4.4/11.4 | 10.2/12.9 |

Percent Aggregation (SEC-HPLC) @ [1 hr/24 hr]-ethyl acetate

| Agitation | 0.05% F127 | 0.2% F127 | 0.05% F127 + T20 | 0.2% F127 + T20 |
|---|---|---|---|---|
| 15 s vortex | 1.4/1.4 | 0.7/0.7 | 2.1/1.9 | 1.0/1.0 |
| 60 s vortex | 1.4/2.0 | 1.5/1.7 | 0.9/1.0 | 1.1/1.1 |

Note:
F127 is PLURONIC™ F127;
T20 is TWEEN™ 20

EXAMPLE 34

Modulation of hGH Release

Protocol.

Stock hGH was microencapsulated into biodegradable microspheres using a two-step process. First, hGH was incorporated into polymer using the FLM process. Specifically, hGH (20 mg/ml) and PLURONIC™ F127 (0.2% w/v) was vortexed in RG502H (Boehringer Inngelheim) or BPI-0.2 (Birmingham Polymers, Inc.) PLGA which was dissolved in ethyl acetate at 5% (w/v) for 15 s and quenched in liquid nitrogen. This frozen emulsion was then lyophilized for 48 hours to remove both the aqueous and organic solvents. In the second step, the lyophilized matrix of dispersed hGH, polymer, surfactant and sucrose was redissolved in ethyl acetate and fabricated into microspheres using phase inversion nanoencapsulation (PIN). Specifically, the matrix was redissolved in ethyl acetate to a polymer solution of 5% (w/v) and poured rapidly into a 50-fold excess of either petroleum ether or 50% isopropanol to produce four microsphere batches. Batch 1: RG502H/isopropanol combination; Batch 2: RG502H/petroleum ether combination; Batch 3: BPI-0.2/isopropanol combination; Batch 4: BPI-0.2/petroleum ether combination. Microspheres formed with petroleum ether extraction were collected by filtration with a 2.7 μm filter and lyophilized 24 hrs for complete removal of solvent. Microspheres formed with isopropanol was collected via lyophilization. All microspheres were produced at 3.5% (w/w) GH loadings. Microspheres (approximately 10 mg) were hydrated in 100 mM NaCl, 25 mM Na Phosphate, 0.05% PLURONIC™ F127 at 50 mg/ml. Microspheres were dispersed (vortexed followed by 5 s bath sonication) and allowed to incubate. At timepoints of 1 hr, 4 hrs, 24 hrs, and 120 hrs, the supernatant was sampled and analyzed for SEC-HPLC quantification of released GH and aggregation.

Results.

GH Release Rate

Figure 5:
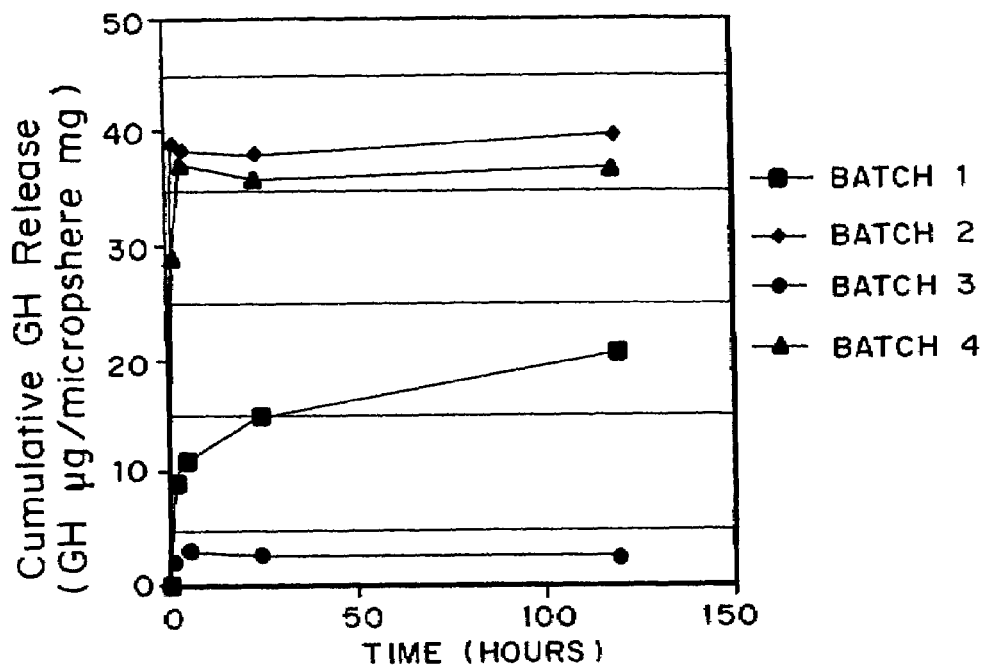
Figure 6:
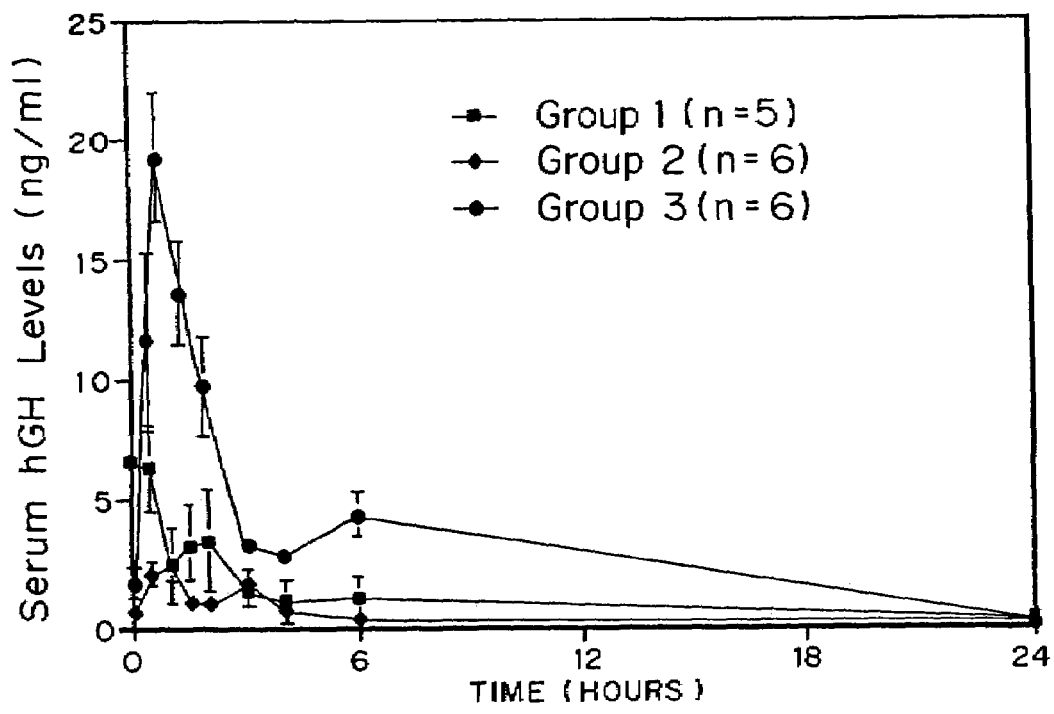

The cumulative release rates (quantified by SEC-HPLC) are shown in FIG. 5. The percent cumulative release calculated from the theoretical GH loading of 3.5% (w/w) is shown in Table 32. First, the use of the more hydrophilic PLGA (50:50) resulted in faster release of GH in both petroleum ether and isopropanol based PIN techniques. Furthermore, within the same polymer type, the use of petroleum ether as the solvent extraction medium resulted in faster release of GH compared to isopropanol. A linear curve fit between 4 and 120 hrs was generated for quantitative characterization of the differences in release rates. Batch 1 exhibited a slow continuous release (approximately 0.1 μg/mg/hr, $r^2=0.93$). Batch 2 exhibited a near total burst at one hour with little release thereafter (approximately 0.02 μg/mg/hr, $r^2=0.79$). Batch 3 exhibited minimal burst at one hour with little release thereafter (approximately 0.01 μg/mg/hr, $r^2=0.75$). Batch 4 exhibited moderate burst at one hour with little release thereafter (approximately 0.04 μg/mg/hr, $r^2=0.32$). Although the $r^2$ coefficient is somewhat variable, there are clear differences across the four batches. The theoretical loading for all four batches was 35.4 μg per mg of microspheres.

TABLE 32

Percent Cumulative Release of GH

|  | Batch 1 | Batch 2 | Batch 3 | Batch 4 |
|---|---|---|---|---|
| 1 hr | 25 | 109 | 5 | 83 |
| 41 hrs | 30 | 108 | 7 | 104 |
| 24 hrs | 43 | 107 | 8 | 103 |
| 120 hrs | 62 | 115 | 10 | 106 |

EXAMPLE 34

Oral GH Delivery with PIN Microspheres

CD male rats (250 to 300 g) were obtained from Charles River Laboratories. Group 1 was fed 1.24 mg of stock GH emulsified in 1 ml of USP corn oil; Group 2 was fed 50 mg of PIN microspheres (2B43099-2.47% Zn-GH in PLGA) in 1 ml of corn oil; Group 3 was fed 50 mg of PIN microspheres (2B51799 - 2.47% Stock GH, 16% FeO in PLGA) in 1 ml of corn oil. Microspheres were suspended in corn oil by vortexing followed by brief (5 s) probe sonication. Stock GH was similarly emulsified in corn oil by vortexing and probe sonication. Animals were fasted overnight, briefly anesthetized with methoxyfluorane, and formulations fed via gavage with an 18-G stainless steel feeding tube and serum from all animals obtained according to the following schedule: −1 hr (pre-feeding control), 0.5 hr, 1 hr, 2 hr, 3 hr, 4 hr, 6 hr, 24 hr, 48 hr, and 72 hr post-feeding. Serum samples obtained via tail bleeding were analyzed for hGH using the hGH specific ELISA (DSL Inc, Webster. Tex.) according to manufacturer's protocols.

The rat serum hGH levels detected following a single dose of hGH is illustrated in 6. Group 1 animals showed detectable levels of hGH with a $C_{max}$ of 3.37±2.14 ng/ml at two hours post-feeding. Group 2 animals also showed detectable levels of hGH with a $C_{max}$ of 2.14±0.65 ng/ml at 1 hour post-feeding. Group 3 animals showed the highest levels of hGH with a $C_{max}$ of 19.23±2.66 ng/ml at 1 hour post-feeding and had consistently higher serum hGH levels at all timepoints up to 24 hours post-feeding.

EXAMPLE 35

Effect of Protein Molecular Weight on Release from Micron-sized PLGA Microspheres The goal of this study was to investigate effects of five proteins of various molecular weight on release kinetics from polymeric microspheres. Proteins were encapsulated at 2% and 7.3% loadings in poly(lactic-co-glycolic acid) (PLGA) by a phase inversion technique. Protein release from microspheres followed the order: lysozyme (14.3 kDa), bovine serum albumin (66 kDa), alcohol dehydrogenase (150 kDa), and thyroglobulin (669 kDa). Carbonic anhydrase (29 kDa) was released more slowly than expected, which could be attributed to its cleaved appearance on SDS-PAGE. Following an initial diffusion phase, all samples demonstrated a lag phase, characterized by curtailed protein release. Between 4 and 8 weeks, only microspheres loaded with the smallest proteins, lysozyme and carbonic anhydrase, exhibited an additional phase of increased protein release, while larger proteins did not. It is concluded that by 8 weeks, the degradation of PLGA had proceeded enough to allow additional release of the smaller proteins, but that further degradation might be necessary to produce the same effect for larger proteins. Additionally, microspheres encapsulating large proteins maintained release rates closest to zero-order. There was no correlation between protein molecular weight and microsphere drug particle size or microsphere pore size.

Materials and Methods

All proteins used in this study were obtained from Sigma. The Micro BCA protein assay reagent kit was purchased from Pierce. Pre-cast polyacrylamide electrophoresis gels and molecular weight marker were obtained from Novex.

Microsphere Fabrication

Microspheres were fabricated from a 2% polymer solution (w/v) of PLGA 50:50 (Mw 12,068) by a phase inversion technique, Mathiowitz, et al., Nature 386, 410–414 (1997). Briefly, two solutions, protein in water and polymer in dichloromethane, were added together at a volume ratio of 1:10. This two-phase system was then probe sonicated at an amplitude of 20% for 30 seconds. Following sonication, the resulting water in oil emulsion was stabilized by immediate freezing in liquid nitrogen followed by lyophilization for 48 hours. The dried product was then resuspended in dichloromethane at a polymer to solvent concentration of 2%. This suspension of solubilized polymer and insoluble protein particles was then quickly introduced into a nonsolvent bath of petroleum ether at a solvent:nonsolvent ratio of 1:50. The resulting microspheres were then collected with a high pressure filtering system. Microspheres were loaded with either 2% or 7.3% (w/w) of one of five proteins: lysozyme (13.4 kDa), carbonic anhydrase (29 kDa), bovine serum albumin (66 kDa), alcohol dehydrogenase (150 kDa), or thyroglobulin (669 kDa). Unloaded microspheres were also fabricated and used as a control for polymer Mw and mass loss.

Protein Release Analysis

Microspheres were divided into 30 mg aliquots and placed in glass scintillation vials. 3 mL of pH 7.0 HPLC-grade water, with 0.03% sodium azide to deter bacterial growth, was added to each vial. The vials were capped and positioned on their sides so that the maximum surface area of each sample would be available for release into water. Samples were incubated at 37° C. for a total of 8 weeks and were assayed at various time points: 0.5, 1, 2, 4, 8, 24, and 72 hours and 1, 2, 4, and 8 weeks. At each timepoint, the samples were centrifuged at 2000 g for 5 minutes, and the supernatants were removed and saved for further analysis. Fresh water was replaced in each vial at each timepoint to allow further protein release. Protein release was assayed with a micro BCA reagent kit and samples read with a Beckman DU-65 spectrophotometer at 562 nm. Values were summed to obtain cumulative release and are reported as per cent release of loaded protein. Supernatants were run on a 4–20% gradient Tris-glycine gel for 90 minutes at 125 V, 35 mA, and 5.0 W to determine the nativity of released proteins. Gels were stained with a Coomassie blue (0.04% G-250, 3.5% perchloric acid) solution.

Polymer degradation analysis

Additional microsphere aliquots of either 10, 30, 50, 60, 70, or 90 mg were placed in microcentrifuge or 15 mL conical tubes and allowed to degrade at 37° C. in HPLC-grade water at concentrations of 10 mg/mL for various amounts of time: 1,2,3,4,5,6 days, and 1,2,3,4,5,6,7, and 8 weeks. At each timepoint, the tubes were centrifuged and the supernatant was removed and discarded. The remaining pellet was frozen and lyophilized, and the final dry weight of the pellet was compared to the original sample weight. For this study, each timepoint was terminal, rather than cumulative. Dried PLGA pellets from the weight loss study were also used to determine molecular weight of degrading microspheres. For each sample, a 5% solution was made in chloroform and analyzed on a Perkin Elmer LC pump model 250 composed of isocratic LC pump model 250, an LC column oven model 101, and LC-30 RI detector, and a 900 series interface computer. Samples were eluted through a PL gel 5 micron mixed column and a 5 micron/50 Å column connected in series at a flow rate of 1.0 mL/min and a temperature of 40° C.

Microsphere Sizing and Imaging

For SEM, samples were mounted and coated for 2.5 minutes with a gold and palladium mixture and examined for morphology and size with a Hitachi S-2700 scanning electron microscope. Thirty microspheres were then randomly selected and measured for diameter using Adobe Photoshop software and results averaged according to microsphere type. For TEM, samples were dehydrated in 100% ethanol, osmicated with $OsO_4$, embedded in LR White embedding media in gelatin capsules, and cured in a 30° C. oven for 3 days. Sections were then cut to a thickness of 95 nm with a diamond knife on a Reichert-Jung Ultracut E microtome. A Philips EM 410 transmission electron microscope was used to examine sections. Diameter averages were taken from a measurement of 14–28 microspheres from a single section and analyzed with Adobe Photoshop. For pore size analysis, a sample of 1 to 3 porous microspheres was selected for each type, although these porous microspheres only made up a minority of the microsphere population. Between 40 and 80 pores were measured per microsphere. To determine protein particle size within the microspheres, 2 mg aliquots of microspheres were dissolved in dichloromethane on a glass coverslip. The resulting polymer film with dispersed solid protein particles was observed by SEM, and particle size analysis performed with Adobe Photoshop. Sizes were averaged among 40–50 particles per microsphere type. For particle size distribution, a 3 mg aliquot of unloaded control microspheres was measured in dry mode with a Sympatec particle size analyzer.

Results

Protein Release Analysis

Figure 7:
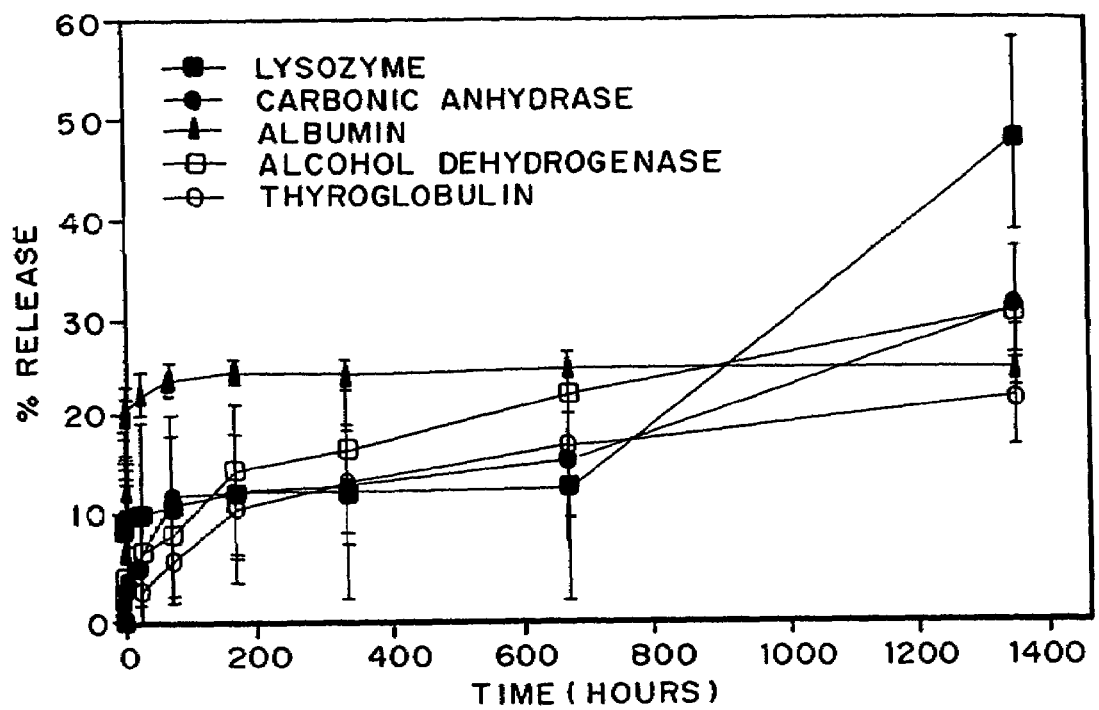
Figure 8:
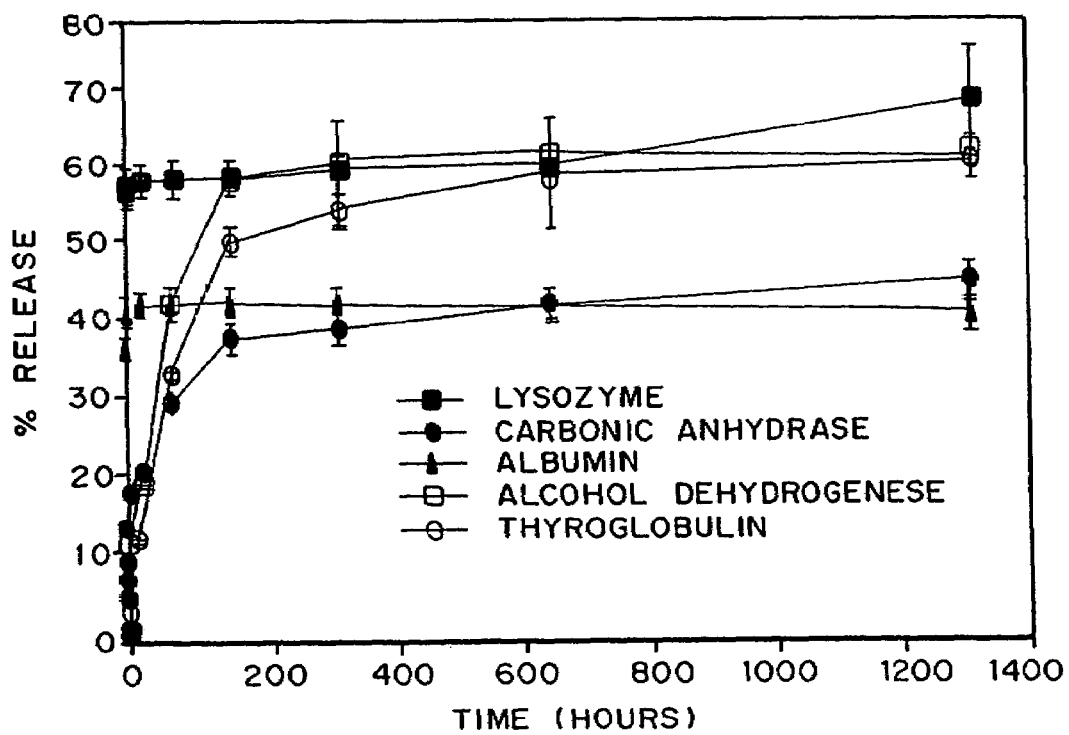

Five proteins commonly used as molecular weight markers, lysozyme, carbonic anhydrase, bovine serum albumin, alcohol dehydrogenase, and thyroglobulin, were encapsulated in PLGA in order to determine how diffusion, polymer degradation, and protein molecular weight affect release from microspheres. Proteins were loaded at levels of 2% and 7.3% (w/w) and were released at sink conditions (10 mg microspheres/mL). These results are shown in FIGS. 7 and 8.

Three phases were observed during release from these formulations. The burst effect, which in this case was part of the first phase, was greatest for lysozyme, followed by bovine serum albumin, alcohol dehydrogenase, carbonic anhydrase, and thyroglobulin from 2% loaded microspheres (FIG. 7). Similar patterns were observed for 7.3% loaded microspheres, with the largest burst from lysozyme, followed by bovine serum albumin, carbonic anhydrase, alcohol dehydrogenase, and thyroglobulin (FIG. 8).

The duration of the first phase, characterized by a quick, nonlinear release, was dependent on the protein size, but independent of the amount of loading. This phase lasted 30 min for lysozyme, 4 hrs for bovine serum albumin, and 1 wk each for alcohol dehydrogenase, thyroglobulin, and carbonic anhydrase. The quantities of protein release during this phase were similar, regardless of the duration of the phase, with the following per cent release from 2% and 7.3% loaded systems, respectively: 9.19% and 56.78% for lysozyme, 20.42% and 41.14% for bovine serum albumin, 23.45% and 58.55% for alcohol dehydrogenase, 11.52% and 50.49% for thyroglobulin, and 12.92% and 38.15% for carbonic anhydrase. The second phase lasted approximately 4 weeks for lysozyme, 3 weeks for 2% carbonic anhydrase and 7 weeks for 7.3% carbonic anhydrase, approximately 8 weeks for bovine serum albumin, and 7 weeks for both alcohol dehydrogenase and thyroglobulin. This lag phase was found for all proteins, regardless of molecular weight. The third phase, a quick additional spurt of protein following the second phase, occurred between 4 and 8 weeks. The existence of this third phase was dependent on protein molecular weight, occurring only for microspheres encapsulating proteins less than or equal to 29 kDa in molecular weight, 2% and 7.3% lysozyme and 2% carbonic anhydrase.

Analysis of released proteins by SDS-PAGE showed that lysozyme and bovine serum albumin released from PLGA microspheres for 30 minutes migrated similarly to native proteins. Lysozyme also migrated similarly after being released for 8 weeks. Released carbonic anhydrase appeared somewhat denatured by 30 minutes and completely denatured by 8 weeks, while released alcohol dehydrogenase appeared completely denatured by 30 minutes. Thyroglobulin was too large to resolve in this system. The nativity of proteins still unreleased from microspheres was not determined.

Polymer Degradation Analysis

Figure 9:
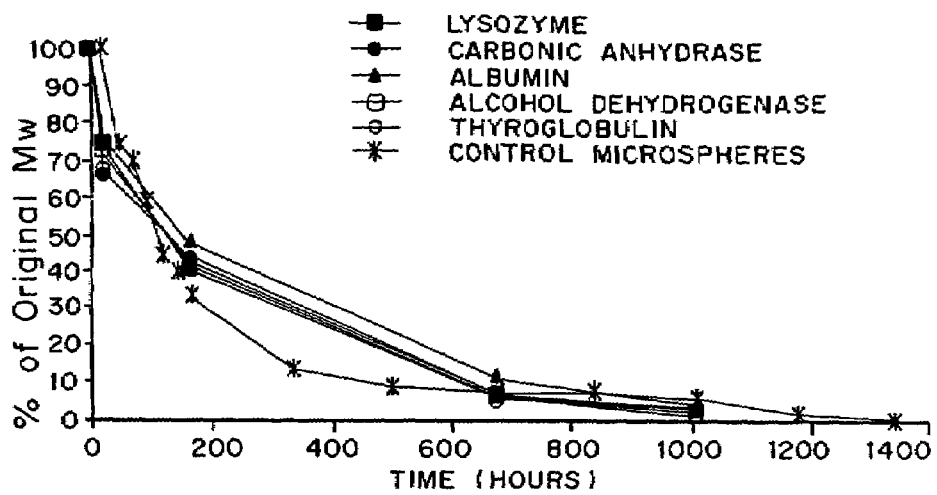
Figure 10:
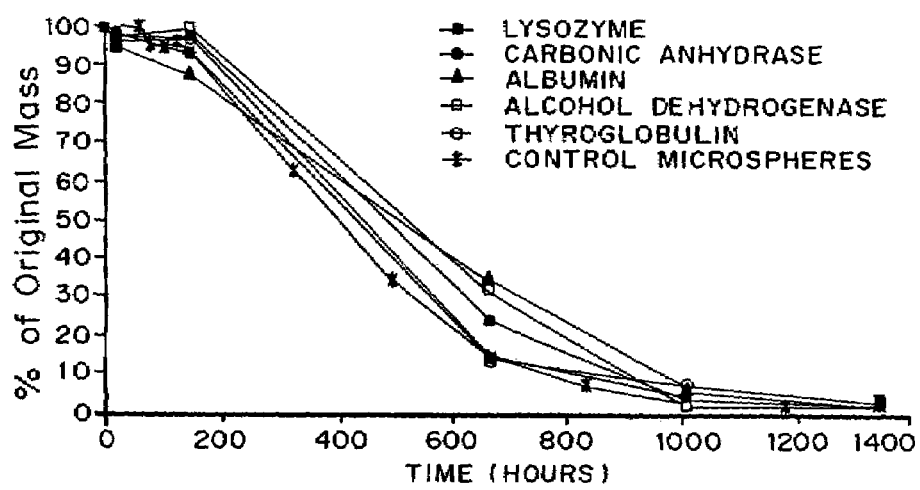

PLGA Mw loss was similar for all samples (FIG. 9). Mw decreased to 70–80% of the original molecular weight (Mw=12,068) by day 1, to 40–50% by 1 week, to 5–10% by 4 weeks, and to 5% by 6 weeks. As expected, mass loss results did not correspond to molecular weight loss (FIG. 10). Sample masses decreased to 95–99% of the original mass by day 1, to 90–98% by 1 week, to 15–35% by 4 weeks, to 5% by 6 weeks, and to 2% by 8 weeks. Supplemental degradation studies of control microspheres revealed that unloaded PLGA microspheres degraded very similarly to those loaded with protein, indicating that encapsulated protein, regardless of molecular weight, does not affect degradation or erosion in this system. The additional data points taken in this study give a better understanding of how all the polymer microspheres are actually degrading over time. Control microspheres decrease almost linearly to 33.4% of their original Mw during the first week. They continue to degrade to 13.2% by the second week, and still retain 7.2% of their original molecular weight by the sixth week. Mass loss shows a decrease to 94.0% by the end of the first week, and a linear drop in mass to 14.7% by the fourth week. Table 33 shows Mw and mass loss for unloaded control microspheres over discrete periods of degradation.

Microsphere Sizing and Imaging

SEM showed that all PLGA microspheres, whether protein-loaded or control, were spherical in shape and did not appear to be aggregated. Type of protein loaded did not appear to affect the morphology of the microspheres. When analyzed with Adobe Photoshop, the SEM micrographs showed no statistically significant differences between average particle size diameters for any of the microsphere groups (Table 34), except for the bovine serum albumin group (0.374 micron±0.08 micron which was significantly higher than the carbonic anhydrase (0.211 micron±0.046 micron), thyroglobulin (0.207 micron±0.044 micron), and control groups (0.196 micron±0.049 micron). Despite these differences, SEM microsphere size did not appear to be dependent on molecular weight of the protein loaded. Particle size analysis was also done on 3 mg aliquots of control microspheres with a Sympatec HELOS model H0849 dry powder analysis system. Microspheres were found to have a volume size distribution median diameter of 2.23 micron by this method. The discrepancy is probably due to slight aggregation of spheres. Morphology of microspheres, as observed by SEM, was shown to be severely degraded by 4 weeks.

TEM micrographs were in agreement with SEM, confirming the spherical nature of specimens in each of the microsphere groups. TEM also provided additional information about the internal structure of microspheres. Unloaded control spheres were granular in appearance, but did not have true pores. Four microsphere groups, however, those loaded with carbonic anhydrase, bovine serum albumin, alcohol dehydrogenase, and thyroglobulin, had diverse populations of microsphere structures. Although the majority of the microspheres in each group appeared dense, each sample contained various types of porous structures, including some that appeared to have an open branched network throughout the microsphere, as well as those that appeared open towards the outer layers and more dense nearer the inner layers of the microsphere. In addition, TEM was also used to obtain an estimate for particle size diameter (Table 33). Although these results did not exactly coincide with those of SEM, they did further strengthen the belief that the microspheres are in the sub-micron to 1 micron range. Results of TEM, and analysis by Adobe Photoshop software, yielded diameter values between 0.819 micron±0.156 micron (alcohol dehydrogenase) and 1.077 micron±0.116 micron (carbonic anhydrase) for the microsphere groups examined. TEM was also a useful tool in determining the average pore size diameter and pore size range. Visible pores are ascribed to protein released from microspheres during processing for TEM and are therefore assumed to be synonymous with interior protein particle size. Overall, pores ranged from 3.22 nm to 151.61 nm (Table 34). Pore size averages were not significantly different from one microsphere type to the next, and they did not appear to show trends dependent on molecular weight of protein. Pores could not be visualized in lysozyme-loaded spheres. Protein particle images obtained by SEM were likewise analyzed and found to have size averages similar to those of the microsphere pores obtained with TEM. Microspheres loaded with alcohol dehydrogenase were found to have protein particles with an average size of 63.5 nm±12.82 nm and those loaded with lysozyme had a very similar average size of 57.48 nm±10.34 nm by SEM. The similarity between protein particle sizes and microsphere pore sizes supports the theory that pores seen by TEM are due to protein encapsulation.

It is concluded that diffusion is the main contributor to protein release in the first phase since masses have only decreased to approximately 97–100% of their original values by the time this phase is complete. A combination of diffusion, degradation, and swelling yield the lag phase. The third phase is predominantly controlled by degradation since diffusion is difficult through the gum that has been formed due to water penetration and subsequent swelling. It is, therefore, believed that the mass loss contributes more than the molecular weight decrease to additional protein release.

The proteins examined in this study span a wide spectrum of molecular weight, with the smallest being 14.3 kDa and the largest 669 kDa. Each of these proteins, when encapsulated by and released from PLGA microspheres, exhibits a release profile that can be attributed to the inherent properties of PLGA, the molecular weight of the protein, and the consequent dependence of the protein release on the diffusion, swelling, and degradation phases of the polymer microspheres. Release from microspheres in this study was not dependent on protein particle size within microspheres. Protein release from microspheres was modulated to a very controlled rate by the close approximation of diffusion and degradation effects for proteins with a molecular weight of 150 kDa or higher. This modulated release lasted for the entirety of the experiment, spanning 56 days.

TABLE 33

Loss of Molecular Weight and Mass

| Time Period | Mw lost | Mass lost |
|---|---|---|
| Up to 1 week | 66.6% | 6.0% |
| 1 week–2 weeks | 20.2% | 31.0% |
| 2 weeks–4 weeks | 5.9% | 48.3% |
| 4 weeks–8 weeks | 7.3% | 12.3% |

TABLE 34

Microsphere Diameter and Pore Size by SEM and TEM

| Microsphere | SEM Diameter (micron) | TEM Diameter (micron) | TEM Pore Size Range (nm) | TEM Pore Size Average (nm) |
|---|---|---|---|---|
| Lysozyme | .260 ± .056 | .959 ± .400 | N/A | N/A |
| Carbonic Anhydrase | .211 ± .046 | 1.077 ± .116 | 3.22–151.61 | 41.23 ± 30.65 |
| Bovine Serum Albumin | .374 ± .080 | .908 ± .207 | 7.90–100.00 | 32.61 ± 10.25 |
| Alcohol Dehydrogenase | .255 ± .070 | .819 ± .156 | 5.26–102.63 | 34.48 ± 18.04 |
| Thyroglobulin | .207 ± .044 | .898 ± .225 | 15.79–60.56 | 32.84 ± 9.99 |
| Control (blank) | .196 ± .049 | .913 ± .273 | N/A | N/A |

Publications cited herein and the material for which they are cited are specifically incorporated by reference. Nothing herein is to be construed as an admission that the invention is not entitled to antedate such disclosure by virtue of prior invention.

Modifications and variations of the methods and devices described herein will be obvious to those skilled in the art from the foregoing detailed description. Such modifications and variations are intended to come within the scope of the appended claims.

We claim:

1. A method for making micronized particles of an agent, comprising:
    (a) dissolving a macromolecular material in an effective amount eta solvent, to form a first solution;
    (b) dissolving the agent in an effective amount of a solvent, to form a second solution;
    (c) adding the second solution to the first solution to form an emulsion and thereby micronize the particles of the agent;
    (d) freezing the emulsion;
    (e) drying by vacuum the frozen emulsion to form solid micronized particles of the agent dispersed in solid macromolecular material; and (f) then, dissolving the macromolecular material having dispersed therein solid micronized particles of the agent in an effective amount of a solvent for the macromolecular material to form a dispersion of solid microparticles of agent in the solvent, wherein the solvent is a non-solvent for the agent.

2. The method of claim 1 further comprising encapsulating the dispersion of solid microparticles of agent in an encapsulating material.

3. The method of claim 1 wherein greater than 90% of the solid particles are less than 0.2 μm in diameter.

4. The method of claim 1 wherein greater than 90% of the solid particles are between 10 nm and 1 μm in diameter.

5. The method of claim 1 wherein the agent is a bioactive agent.

6. The method of claim 5 wherein the bioactive agent is a protein.

7. The method of claim 6 wherein the protein is a growth hormone.

8. The method of claim 6 wherein the protein is an osteoprotegrenin.

9. The method of claim 5 wherein the agent is selected from the group consisting of peptides, antibiotics, nucleotide molecules, and synthetic drugs.

10. The method of claim 1 wherein the macromolecular material is a polymer.

11. The method of claim 10 wherein the polymer is selected from the group consisting of polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide), poly(lactide-co-caprolactone), and blends and copolymers thereof.

12. The method of claim 1 wherein step (d) utilizes lyophilization.

13. The method of claim 2 wherein the encapsulation is conducted using a process selected from the group consisting of interfacial polycondensation, spray drying, hot melt microencapsulation, and phase separation techniques.

14. The method of claim 13 wherein the phase separation technique is selected from the group consisting of solvent extraction, solvent evaporation, and phase inversion.

15. The method of claim 14 wherein the phase inversion technique comprises:
introducing the dispersion into a nonsolvent, wherein the volume ratio of solvent:nonsolvent is at least 1:40, to cause the spontaneous formation of a microencapsulated product, wherein the solvent and the nonsolvent are miscible.

16. The method of claim 15 wherein the solvent and non-solvent are slightly miscible.

17. The method of claim 15 wherein the volume ratio of solvent:nonsolvent is between 1:50 and 1:200.

18. The method of claim 15 wherein the macromolecular material is dissolved in the solvent at a concentration of less than 10% weight per volume and wherein viscosity of the macromolecular material in the solvent is less than 3.5 cP.

19. The method of claim 17 wherein the concentration of the macromolecular material in the solvent is between 0.5 and 5% weight per volume.

20. The method of claim 6 wherein freezing of the emulsion is performed following addition of the agent to the solution at a rate effective to avoid denaturing of the protein.

21. The method of claim 2 wherein the encapsulating material is a biocompatible polymer.

22. The method of claim 21 wherein the biocompatible polymer is selected from polyesters, polyanhydrides, polystyrenes, poly(ortho)esters, copolymers thereof, and blends thereof.

23. The method of claim 1 wherein greater than 90% solid particles are less than 1 μm in diameter.

24. The method of claim 1, farther comprising separating the solid micronized particles of agent from the macromolecular material.

* * * * *

UNITED STATES PATENT AND TRADEMARK OFFICE
CERTIFICATE OF CORRECTION

PATENT NO. : 7,029,700 B2 Page 1 of 1
APPLICATION NO. : 09/760046
DATED : April 18, 2006
INVENTOR(S) : Edith Mathiowitz, Yong S. Jong and Jules S. Jacob It is certified that error appears in the above-identified patent and that said Letters Patent is hereby corrected as shown below:

Column 46, line 58, replace "eta" with --of a --.
Column 47, line 30, delete "poly(butic acid)".
Column 48, line 35, replace "farther" with --further--.

Signed and Sealed this

Second Day of October, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,029,700 B2 | Page 1 of 1 |
| APPLICATION NO. | : 09/760046 | |
| DATED | : April 18, 2006 | |
| INVENTOR(S) | : Edith Mathiowitz et al. | |

It is certified that error appears in the above-identified patent and that said Letters Patent is hereby corrected as shown below:

In the Specification

Column 1, insert the following heading prior to the paragraph at lines 3-4 --CROSS-REFERENCE TO RELATED APPLICATIONS--.

Column 1, lines 5-7, replace the paragraph "The United Stated government has certain rights in this application by virtue of National Institutes of Health grant #1R01GM55245-01."

with the following heading and paragraph:

--GOVERNMENT SUPPORT
This invention was made with government support under NIH: R01 GM552451 awarded by the National Institutes of Health. The government has certain rights in the invention.--

Signed and Sealed this
Seventeenth Day of June, 2014

Michelle K. Lee
*Deputy Director of the United States Patent and Trademark Office*